(12) United States Patent
Robblee

(10) Patent No.: US 12,360,119 B2
(45) Date of Patent: *Jul. 15, 2025

(54) METHODS RELATED TO BIOLOGICS

(71) Applicant: Momenta Pharmaceuticals, Inc., Titusville, NJ (US)

(72) Inventor: John Robblee, Concord, MA (US)

(73) Assignee: MOMENTA PHARMACEUTICALS, INC., Titusville, NJ (US)

( * ) Notice: Subject to any disclaimer, the term of this patent is extended or adjusted under 35 U.S.C. 154(b) by 216 days.

This patent is subject to a terminal disclaimer.

(21) Appl. No.: 18/331,803

(22) Filed: Jun. 8, 2023

(65) Prior Publication Data

US 2023/0324406 A1 Oct. 12, 2023

Related U.S. Application Data

(63) Continuation of application No. 16/067,411, filed as application No. PCT/US2016/068871 on Dec. 28, 2016, now Pat. No. 11,719,704.

(60) Provisional application No. 62/273,337, filed on Dec. 30, 2015.

(51) Int. Cl.
| | |
|---|---|
| *G01N 33/68* | (2006.01) |
| *C07K 14/54* | (2006.01) |
| *C07K 16/24* | (2006.01) |
| *C12P 21/00* | (2006.01) |

(52) U.S. Cl.
CPC ......... *G01N 33/6854* (2013.01); *C07K 14/54* (2013.01); *C07K 14/5434* (2013.01); *C07K 16/244* (2013.01); *C12P 21/005* (2013.01); *C07K 2317/14* (2013.01); *C07K 2317/21* (2013.01); *C07K 2317/30* (2013.01); *C07K 2317/41* (2013.01); *G01N 2440/38* (2013.01)

(58) Field of Classification Search
CPC ................................................. G01N 33/6854
See application file for complete search history.

(56) References Cited

U.S. PATENT DOCUMENTS

| | | | |
|---|---|---|---|
| 4,868,116 A | 9/1989 | Morgan et al. | |
| 4,980,286 A | 12/1990 | Morgan et al. | |
| 5,013,556 A | 5/1991 | Woodle et al. | |
| 5,308,341 A | 5/1994 | Chanoch | |
| 5,641,640 A | 6/1997 | Hanning | |
| 5,807,715 A | 9/1998 | Morrison et al. | |
| 6,146,361 A | 11/2000 | DiBiasi et al. | |
| 6,192,891 B1 | 2/2001 | Gravel et al. | |
| 6,200,296 B1 | 3/2001 | Dibiasi et al. | |
| 6,277,099 B1 | 8/2001 | Strowe et al. | |
| 6,302,855 B1 | 10/2001 | Lav et al. | |
| 7,556,615 B2 | 7/2009 | Pettis et al. | |
| 11,719,704 B2 | 8/2023 | Robblee | |
| 2011/0045581 A1 | 2/2011 | Collao Olivares et al. | |
| 2013/0123126 A1 | 5/2013 | Collins et al. | |
| 2014/0271622 A1 | 9/2014 | Prentice | |
| 2014/0359902 A1 | 12/2014 | Ariaans et al. | |
| 2015/0158907 A1 | 6/2015 | Zhou et al. | |
| 2015/0204884 A1 | 7/2015 | Robblee et al. | |
| 2015/0252108 A1 | 9/2015 | Washburn et al. | |
| 2016/0032232 A1 | 2/2016 | Khan | |
| 2016/0289628 A1 | 10/2016 | Cizek et al. | |
| 2020/0199525 A1 | 6/2020 | Boon et al. | |
| 2021/0222109 A1 | 7/2021 | Yin et al. | |
| 2022/0033487 A1 | 2/2022 | Zang | |
| 2022/0081479 A1 | 3/2022 | Zang | |

FOREIGN PATENT DOCUMENTS

| | | |
|---|---|---|
| CN | 105378086 A | 3/2016 |
| CN | 105779394 A | 7/2016 |
| CN | 106029871 A | 10/2016 |
| CN | 107109455 A | 8/2017 |
| WO | 1989002468 A1 | 3/1989 |
| WO | 1989007136 A2 | 8/1989 |
| WO | 1991011508 A1 | 8/1991 |
| WO | 1992007573 A1 | 5/1992 |
| WO | 2002030954 A1 | 4/2002 |
| WO | 2004060407 A1 | 7/2004 |
| WO | 2008128216 A1 | 10/2008 |
| WO | 2008128218 A1 | 10/2008 |
| WO | 2008128219 A1 | 10/2008 |
| WO | 2008128220 A1 | 10/2008 |
| WO | 2008128221 A1 | 10/2008 |
| WO | 2008128222 A1 | 10/2008 |
| WO | 2008128225 A1 | 10/2008 |
| WO | 2008128227 A1 | 10/2008 |
| WO | 2008128228 A1 | 10/2008 |
| WO | 2008128230 A1 | 10/2008 |
| WO | 2008130924 A2 | 10/2008 |
| WO | 2008130926 A2 | 10/2008 |
| WO | 2010071817 A2 | 6/2010 |
| WO | 2010071824 A2 | 6/2010 |
| WO | 2010085251 A1 | 7/2010 |
| WO | 2010089151 A1 | 8/2010 |

(Continued)

OTHER PUBLICATIONS

European Medicines Agency Evaluation of Medicines for Human Use "Assment Report for Stelara", Retrieved from the Internet:// www.ema.europa.eu/documents/assessment-report/stelara-epar-public-assessment-report_en.pdf, retrieved on Jun. 24, 2019.

(Continued)

*Primary Examiner* — Prema M Mertz

(74) *Attorney, Agent, or Firm* — Troutman Pepper Locke LLP; Mark R. Bell; Megan T. O'Gara

(57) ABSTRACT

The present disclosure relates to the characterization and production of biologics.

14 Claims, 3 Drawing Sheets

Specification includes a Sequence Listing.

(56) References Cited

FOREIGN PATENT DOCUMENTS

| | | |
|---|---|---|
| WO | 2011069056 A2 | 6/2011 |
| WO | 2011127322 A1 | 10/2011 |
| WO | 2013181575 A2 | 12/2013 |
| WO | 2013181586 A2 | 12/2013 |
| WO | 2014193973 A2 | 12/2014 |
| WO | 2015105926 A1 | 7/2015 |
| WO | 2017021493 A1 | 2/2017 |
| WO | 2017117218 A1 | 7/2017 |
| WO | 2017194605 A1 | 11/2017 |
| WO | 2018024770 A1 | 2/2018 |
| WO | 2020051042 A1 | 3/2020 |
| WO | 2020142275 A1 | 7/2020 |

OTHER PUBLICATIONS

Ghaderi, et al., Production platforms for biotherapeutic glycoprotins. Occurence, inpact, and challenges of non-human sialylation, Biotechnol Genet Eng Rev., (2012) 28:147-75.

Sanchez-De Melo, et al., N-glycosylation profile analysis of Trastuzumab biosimilar candidates by Normal Phase Liquid Chromatography and MALD-TOF MS approaches, J Proteomics, (2015) 12(ptB):225-33.

Rudikoff et al., "Single Amino Acid Substitution Altering Antigen-Binding Specificity", Proc Natl Acad Sci USA (1982) 79 (6): 1979-83.

Janeway et al., "Immuno Biology the Immune System in Hearlth and Disease", Immunobiology, 3rd edition, (1997) Publishing Inc., pp. 3:1-3:11.

Edwards et al., "The Remarkable Flexibiltiy of the Human Antibody Repertoire; Isolation of Over One Thousand Different Antibodies to a Single Protein, BLyS", J Mol Biol (2003) 14; 334(1): pp. 103-118.

Lloyd et al., "Modelling the human immune response: performance of 10" Human antibody repertoire against a broad panel of therapeutically relevant antigens", Protein Eng Des Sel (2009) 22(3): pp. 159-168, doi: 10.1093/protein/gzn058.epub Oct. 29, 2008.

Goel et al., "Plasticity within the Antigen-Combining Site May Manifest as Molecular mimicry in the Humoral Immune Response" J Immunol (2004) 173(12):7358-67.

Kanyavuz et al., "Breaking the law: unconventional strategies for antibody diversification" Nat Rev Immunol (2019) 19 (6):355-368. doi:10.1038/S41577-019-0126-7.

D'Angelo et al., "Many Routes to an Antibody Heavy-Chain CDR3: Necessary, Yet Insufficient, for Specific Binding", Front Immunol. (2018) 8;9:395. doi:103389/fimmu.2018.00395.eCollection 2018.

Non-Final Office Action for U.S. Appl. No. 16/067,411 dated Apr. 12, 2022.

Gooch et al., "Shear Sensitivity in animal cell culture" Current Opinion in Biotechnology (1993) 4:193-196.

Zhu et al, "NSO Cell Damage by High Gas Velocity Sparging in Protein-Free and Cholesterol-Free Cultures" Biotechnology and Bioengineering, (2008) vol. 101, No. 4, pp. 751-760.

Hamm et al, Characterizatin of N-Linked Blycosylation in a Mnoclonal Antibody Producted in NS0 Cells Using Capillary Electrophonesis with Laser-Induced Fluroescence Detection, Pharmaceuticals, (2013) 6:393-406.

Haselberg et al., "Heterogeneity assessment of antibody-derived therapeutics at the intact and middle-up level by lo-flow sheathless capillary electrophoresis-mass spectrometry", Analytica Chimica Acta (2018), 1044:181-190.

Liu, "Antibody Glycosylation and Its Impact on the Pharmacokinetics and Parmacodynamics of Monoclonal Antibodies and Fc-Fusion Proteins", Journal of pharmaceutical Sciences (2015) 104:1866-1844.

Liu et al., "Pharmacokinetics of monoclonal antibodies and Fc-fusion proteins" (2018) 9(1):15-32.

Mimura, et al., "Glycosylation engineering of therapeutic IgG antibodies: challenges for the safety, funtionality and efficacy", Protein Cell (2018) (1):47-62.

Zhang et al., "Challenges of glycosylation analysis and control: an integrated apporach to producing potimal and consistant therapeutic drugs", Drug Discovery Today (2016) 21(5)p. 740-765.

Hincal, "An Introduction to Safety Issues in Biosimilars/Follow-On Biopharmaceuticals", J. Med. CBR Def. (2009) 7:1-18.

Nowicki, "Basic Facts about Biosimilars", Kidney Blood Press (2007) 30:267-272.

Anumula, "Advances in fluorescence derivatization methods for high-performance liquid chromatographic analysis of glycoprotein carbohydrates" Anal. Biochem., (2006) 350(1):1-23.

Goetze et al., "High-mannose glycans on the Fc region of therapeutic IgG antibodies increase serum clearance in humans", Glycobiol (2011) 21:949-959.

Xie et al., "Rapid comparison of a candidate biosimilar to an innovator monoclonal antibody with advanced liquid chormatography and mass spectrometry technologies" (2010) mAbs, 2:379-394.

Chen, "Analysis of N-glycan from recominant immunoglobulin G by on-line reversed-phase high-performance liquid chromatography/ mass spectrometry", Anal. Biochem., (2007) 370:147-161.

Forrer et al., "Chip-based gel electrophoreses method for the quantification of hallf-antibody species in IgG4 and their by- and degradation products", Anal. Biochem., (2004) 334:81-88.

Hokke et al., "Sialylated carbohydrate chains of recombinant human glycoproteins expressed in Chiese hamster ovary cells contain traces of N-glycolylneuraminic acid" FEBS Lett., (1990) 275:9-14.

Sekhon et al., "Biosimilars: an overview" Biosimilars, (2011) 1:1-11.

Schellekens et al., "Clinical comparability and European biosimilar regulations", Nat Biotechnol . . . (2010) 28:28-31.

Ahn et al., "Separation of 2-aminobenzamide labeled glycans using hydrophilic interaction chromatography columns packed with 1.7 ?m sorbent" Chrom. B, (2010) 878:403-408.

Hara et al., "Determination of Mono-O-acetylated N-Acetylneuraminic", Anal Biochem., (1989) 179:162-166.

Bitter et al., "Expression and Secretion Vectors for Yeast" Methods in Enzymol. (1987) 153:516-544.

Chen et al., "Gas-phase oligosaccharide nonreducing end (GONE) sequencing and structural analysis by reversed phase hplc/mass spectrometry with polarity switching" J. Am. Soc. Mass Spectrom., (2009) 20:1821-1833.

Dick et al. "C-terminal lysine variants in fully human monoclonal antibodies: Investigation of test methods and possible causes", Biotechnology and Bioengineering (2008) 100:1132-1143.

Roger, "Biosimilars: current status and future directions", Expert Opin. Bio. Ther., (2010) 10(7):1011-1018.

Logan et al., "Adenovirus tripartite leader sequence enhances translation of mRNAs late after infection", Proc. Natl. Acad. Sci. USA (1984) 8 1:3655-3659.

Shang et al., "Development and Application of a Robust N-Glycan Profiling Method for Heightened Characterization of Monoclonal Antibodies and Related Glycoproteins" J. Pharm. Sciences, (2014) 103:1967-1978.

Notice of Allowance for U.S. Appl. No. 16/067,411 dated Mar. 8, 2023.

International Search Report and Written Opinion for International PCT Application No. PCT/US2016/068871 dated Apr. 13, 2017.

European Search Report for European Patent Application No. 16882558.6 dated Jul. 8, 2019.

International Search Report and Written Opinion for International PCT Application No. PCT/US2019/048594 dated Nov. 15, 2019.

European Search Report for European Patent Application No. 19857341.2 dated Jun. 7, 2022.

International Search Report and Written Opinion for International PCT Application No. PCT/US2019/067916 dated Apr. 14, 2020.

European Search Report for European Patent Application No. 19907232.3 dated Aug. 18, 2022.

Final Office Action for U.S. Appl. No. 16/067,411 dated Oct. 7, 2022.

Fournier et al., "A Review of Glycan Analysis Requirements," BioPharm International (Oct. 1, 2015) vol. 28, No. 10, pp. 32-37.

Gilmar et al., "Rapid Assessment of Molecular Similarity between a Candidate Biosimilar and an Innovator Monoclonal Anitbody

(56) References Cited

OTHER PUBLICATIONS

Using Complementary LC-MS Methods," BioPharm International (Aug. 1, 2010) vol. 23, No. 8, Suppl. 1, pp. 16-21.
Hallewell et al., "Genetically Engineered Polymers of Human CuZn Superoxide Dismutase," J. Biol. Chem. (1989) vol. 264, No. 9, pp. 5260-5268.
Corrected Notice of Allowability for U.S. Appl. No. 16/067,411 dated Jun. 14, 2023.
Restelli et al., "The Effect of Cell Culture Parameters on Protein Glycosylation," Cell Engineering (Jan. 1, 2002) vol. 3, pp. 61-92.
Amano et al., "Mammalian cell culture tank design by computational fluid dynamics," Hitachi Review (2007) vol. 89(5), pp. 34-37.
Non-final Office Action mailed Apr. 24, 2024 received in U.S. Appl. No. 17/273,004.
Chao et al., "Research of Therapeutic Antibody Glycosylation and Its Applications," Shandong Chemical Industry (2013) vol. 42(10), pp. 54-57, 61.
European Search Report for European Patent Application No. 23201801.0 dated Feb. 16, 2024.
Zhang et al., "Glycan Analysis of Therapeutic Glycoproteins," mAbs (Nov. 24, 2015) vol. 8, No. 2, pp. 205-215.
Alfthan et al., "Properties of a Single-Chain Antibody Containing Different Linker Peptides" Protein Eng. (1995) vol. 8, Issue 7, pp. 725-731.
McCracken et al., "Control of Galactosylated Glycoforms Distribution in the Cell Culture System," Biotechnology Progress (2014) vol. 30, No. 3, pp. 547-553.
Pacis et al., "Effects of Cell Culture Conditions on Anitbody N-Linked Glycosylation—What Affects High Mannose 5 Glycoform," Biotech. & Bioeng. (2011) vol. 108, No. 10, pp. 2348-2358.
Fan et al., "A Multi-Pronged Investigation into the Effect of Glucose Starvation and Culture Duration on Fed-Batch CHO Cell Culture," Biotech. & Bioeng. (2015) vol. 108, No. 10, pp. 2172-2184.
Loebrich et al., "Comprehensive manipulation of glycosylation profiles across development scales," MABS (2019) vol. 11(2), pp. 335-349.
Non-final Office Action mailed Sep. 10, 2024 received in U.S. Appl. No. 17/419,480.

Ustekinumab Heavy Chain AA Sequence:

EVQLVQSGAEVKKPGESLKISCKGSGYSFTTYWLGWVRQMPGKGLDWIGIMSPVDSDI
RYSPSFQGQVTMSVDKSITTAYLQWNSLKASDTAMYYCARRRPGQGYFDFWGQGTLV
TVSSASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKKVEPKSCDKTHTCPPCPAPE
LLGGPSVFLFPPKPKDTLMISRTPEVTCVVVDVSHEDPEVKFNWYVDGVEVHNAKTKPR
EEQYNSTYRVVSVLTVLHQDWLNGKEYKCKVSNKALPAPIEKTISKAKGQPREPQVYTL
PPSRDELTKNQVSLTCLVKGFYPSDIAVEWESNGQPENNYKTTPPVLDSDGSFFLYSKLT
VDKSRWQQGNVFSCSVMHEALHNHYTQKSLSLSPGK (SEQ ID NO:1)

FIG. 1

Ustekinumab Light Chain AA Sequence:

DIQMTQSPSSLSASVGDRVTITCRASQGISSWLAWYQQKPEKAPKSLIYAASSLQSGVPS
RFSGSGSGTDFTLTISSLQEDFATYYCQQYNIYPYTFGQGTKLEIKRTVAAPSVFIFPPSDE
QLKSGTASVVCLLNNFYPREAKVQWKVDNALQSGNSQESVTEQ (SEQ ID NO:2)

FIG. 2

| Parameter # | Parameter  ⬤ Mannose  ◀ Fucose  ■ GlcNAc  ○ Galactose  ◆ NeuGc | Reference Criterion (rule) |
|---|---|---|
| 1 | ("Glycan 1") | >6%* |
| 2 | ("Glycan 2") | >3%* |
| 3 | ("Glycan 3") | >7%* |
| 4 | ("Glycan 4") | >0.5%* |

* For any given parameter, precent refers to the number of moles of PNGase F-released glycan X relative to total moles of PNGase F-released glycan detected as disclosed in Table 1, wherein X represents the parameter of interest (e.g., parameter(s) 1-4).

FIG. 3

\* Percent refers to the number of moles of PNGase F-released glycan X relative to total moles of PNGase F-released glycan detected, wherein X represents the glycan structure of interest.

METHODS RELATED TO BIOLOGICS

CROSS REFERENCE TO RELATED APPLICATIONS

The present application is a continuation of U.S. patent application Ser. No. 16/067,411, filed Jun. 29, 2018, which is a national stage application under 35 U.S.C. § 371 of PCT Application No. PCT/US2016/068871, filed Dec. 28, 2016, which claims the benefit of U.S. Provisional Application. No. 62/273,337, filed on Dec. 30, 2015, the contents of which are herein incorporated by reference in their entirety.

SEQUENCE LISTING

This application contains a Sequence Listing filed electronically as an XML file named "258199_040011_ST26.xml", which was created on Jun. 8, 2023, and is 4,193 bytes in size. The Sequence Listing is hereby incorporated by reference in its entirety.

FIELD OF THE INVENTION

This disclosure provides compositions and methods related to ustekinumab.

BACKGROUND

Ustekinumab (marketed under the trade name STELARA® in the United States and Europe) is a genetically engineered human monoclonal IgG1 kappa antibody directed against the p40 subunit of both IL-12 and IL-23. Ustekinumab has an approximate molecular weight of 148 kD.

STELARA® is provided as a sterile, clear, colorless to slightly yellow, preservative-free liquid concentration typically for subcutaneous administration. STELARA® is supplied at a concentration of 90 mg/mL in either 45 mg (0.5 mL) or 90 mg (1 mL) single-use vials or single-use prefilled syringes. The product is formulated in 1 mg/mL L-histidine and L-histidine monohydrochloride monohydrate, 0.04 mg/mL Polysorbate 80, 38 mg/mL sucrose, and water for injection. The pH of the product is 5.7-6.3. (See STELARA® Prescribing Information dated March 2014, Janssen Biotech Inc.)

SUMMARY OF THE INVENTION

The present disclosure provides, in part, methods for evaluating, identifying, analyzing and/or producing (e.g., manufacturing) ustekinumab. In some instances, methods herein allow highly resolved evaluation of ustekinumab useful for, inter alia, manufacturing ustekinumab, characterizing ustekinumab, identifying, analyzing and/or confirming ustekinumab, monitoring the structure of ustekinumab, comparing ustekinumab preparations made over time or made under different conditions, and/or controlling the structure of ustekinumab.

In certain aspects, the disclosure provides methods of evaluating a glycoprotein preparation (e.g., such as a glycoprotein drug substance or drug product preparation). Such methods can include evaluating the glycoprotein preparation for the presence, absence, and/or level of sialylated glycans (e.g., acquiring information (e.g., a value) pertaining to sialylated glycans). In some instances, such methods can include evaluating the glycoprotein preparation for the presence, absence, level and/or ratio of one or more (e.g., two or more when working with ratios) ustekinumab-specific parameters (i.e., acquiring information (e.g., value(s)) pertaining to the ustekinumab-specific parameters). Such methods can also optionally include providing, e.g., acquiring, a determination of whether the presence, absence, level and/or ratio of sialylated glycans and/or one or more ustekinumab-specific parameters evaluated meets a reference criteria for the sialylated glycans and/or one or more ustekinumab-specific parameters, which determination includes, for example, comparing the presence, absence, level and/or ratio of sialylated glycans and/or one or more ustekinumab-specific parameters evaluated with the reference criteria and/or confirming that the presence, absence, level or ratio of sialylated glycans and/or one or more ustekinumab-specific parameters evaluated has a defined (e.g., predefined) relationship with the reference criteria. In some instances, the one or more (e.g., two or more when working with ratios) ustekinumab-specific parameters evaluated include one or more (e.g., 1, 2, 3, or 4) parameters disclosed in FIG. 3 (e.g., Glycan 1, Glycan 2, Glycan 3, or Glycan 4 listed in FIG. 3).

In some aspects, the disclosure provides methods of evaluating a ustekinumab drug product. Such methods can include a first step of providing (e.g., producing or expressing (e.g., in small scale or large scale cell culture) or manufacturing) or obtaining (e.g., receiving and/or purchasing from a third party (including a contractually related third party or a non-contractually-related (e.g., an independent) third party) a glycoprotein preparation from a ustekinumab drug product; and a second step of acquiring (e.g., detecting, measuring, receiving, or obtaining, as discussed subsequently herein) a value for level of sialylated glycans (e.g., detectable sialylated glycans) in the glycoprotein preparation. In some instances, the acquired (e.g., detected, measured, received, or obtained) value for level of sialylated glycans is about 5%, 10%, 15%, 20%, 25% 30%, 35%, 40%, 50%, 10-20%, 20-30%, 30-40%, 40-50%, 10-50%, 20- 50%, 30-50%, 40-50%, or 25-35%.

In some instances, the second step comprises acquiring (e.g., detecting, measuring, receiving, or obtaining, as discussed subsequently herein) a value for one or more parameters listed in FIG. 3 (e.g., Glycan 1, Glycan 2, Glycan 3, or Glycan 4 listed in FIG. 3). In some instances, the acquired (e.g., detected, measured, received, or obtained) value for parameter 1 (e.g., Glycan 1) is about 5-20% (e.g., about 5-10%, 10-20%, 7-12%, 5%, 6%, 7%, 8%, 9%, 10%, 11%, 12%, 13%, 14%, or 15%); the acquired value for parameter 2 (e.g., Glycan 2) is about 2-10% (e.g., about 2-5%, 5-10%, 3-7%, 2%, 3%, 4%, 5%, 6%, 7%, 8%, 9%, or 10%); the acquired value for parameter 3 (e.g., Glycan 3) is about 5-20% (e.g., about 5-10%, 10-20%, 7-12%, 5%, 6%, 7%, 8%, 9%, 10%, 11%, 12%, 13%, 14%, or 15%), and/or the acquired value for parameter 4 (e.g., Glycan 4) is about 0.5-5% (e.g., about 0.5-2.5%, 2.5-5%, 0.5%, 1%, 1.5%, 2%, or 2.5%). In some instances, the acquired value for one or more parameter listed in FIG. 3 (e.g., Glycan 1, Glycan 2, Glycan 3, or Glycan 4 listed in FIG. 3) for the glycoprotein preparation meets the reference criterion shown in FIG. 3.

In some instances, methods can further include, e.g., one or more of: memorializing the level of sialylated glycans and/or value for one or more parameter listed in FIG. 3 using a recordable medium (e.g., on paper or in a computer readable medium, e.g., in a Certificate of Testing, Certificate of Analysis, Material Safety Data Sheet (MSDS), batch record, or Certificate of Analysis (CofA)); informing a party or entity (e.g., a contractual or manufacturing partner, a care giver or other end-user, a regulatory entity, e.g., the FDA or other U.S., European, Japanese, Chinese or other governmental agency, or another entity, e.g., a compendial entity (e.g., U.S. Pharmacopoeia (USP)) or insurance company) of the level of sialylated glycans and/or value for one or more parameter listed in FIG. 3 (e.g., Glycan 1, Glycan 2, Glycan 3, or Glycan 4 listed in FIG. 3).

In some aspects, the disclosure provides methods of evaluating an antibody. Such methods can include a first step of providing (e.g., producing or expressing (e.g., in small scale or large scale cell culture) or manufacturing) or obtaining (e.g., receiving and/or purchasing from a third party (including a contractually related third party or a non-contractually-related (e.g., an independent) third party) a glycoprotein preparation from a recombinant antibody composition having (i) a first amino acid sequence with at least 85% identity (e.g., about 90, 95, 98, or 100% identity) to SEQ ID NO:1, or a first amino acid sequence with at least 85% identity (e.g., about 90, 95, 98, or 100% identity) to SEQ ID NO:1 and lacking 1, 2, 3, 4, or 5 amino acid residues at the amino and/or carboxyl terminus and (ii) a second amino acid sequence with at least 85% identity (e.g., about 90, 95, 98, or 100% identity) to SEQ ID NO:2, or a second amino acid sequence with at least 85% identity (e.g., about 90, 95, 98, or 100% identity) to SEQ ID NO:2 and lacking 1, 2, 3, 4, or 5 amino acid residues at the amino and/or carboxyl terminus; and a second step of acquiring (e.g., detecting, measuring, receiving, or obtaining, as discussed subsequently herein) a value for level of sialylated glycans (e.g., detectable sialylated glycans) in the glycoprotein preparation. In some instances, the acquired (e.g., detected, measured, received, or obtained) value for level of sialylated glycans is about 5%, 10%, 15%, 20%, 25% 30%, 35%, 40%, 50%, 10-20%, 20-30%, 30-40%, 40-50%, 10-50%, 20-50%, 30-50%, 40-50%, or 25-35%.

In some instances, the second step comprises acquiring (e.g., detecting, measuring, receiving, or obtaining, as discussed subsequently herein) a value for one or more parameter listed in FIG. 3 (e.g., Glycan 1, Glycan 2, Glycan 3, or Glycan 4 listed in FIG. 3). In some instances, the acquired (e.g., detected, measured, received, or obtained) value for parameter 1 (e.g., Glycan 1) is about 5-20% (e.g., about 5-10%, 10-20%, 7-12%, 5%, 6%, 7%, 8%, 9%, 10%, 11%, 12%, 13%, 14%, or 15%); the acquired value for parameter 2 (e.g., Glycan 2) is about 2-10% (e.g., about 2-5%, 5-10%, 3-7%, 2%, 3%, 4%, 5%, 6%, 7%, 8%, 9%, or 10%); the acquired value for parameter 3 (e.g., Glycan 3) is about 5-20% (e.g., about 5-10%, 10-20%, 7-12%, 5%, 6%, 7%, 8%, 9%, 10%, 11%, 12%, 13%, 14%, or 15%), and/or the acquired value for parameter 4 (e.g., Glycan 4) is about 0.5-5% (e.g., about 0.5-2.5%, 2.5-5%, 0.5%, 1%, 1.5%, 2%, or 2.5%). In some instances, the acquired value for one or more parameter listed in FIG. 3 (e.g., Glycan 1, Glycan 2, Glycan 3, or Glycan 4 listed in FIG. 3) for the glycoprotein preparation meets the reference criterion shown in FIG. 3.

In some instances, methods can further include, e.g., one or more of: memorializing the level of sialylated glycans and/or value for one or more parameters listed in FIG. 3 using a recordable medium (e.g., on paper or in a computer readable medium, e.g., in a Certificate of Testing, Certificate of Analysis, Material Safety Data Sheet (MSDS), batch record, or Certificate of Analysis (CofA)); informing a party or entity (e.g., a contractual or manufacturing partner, a care giver or other end-user, a regulatory entity, e.g., the FDA or other U.S., European, Japanese, Chinese or other governmental agency, or another entity, e.g., a compendial entity (e.g., U.S. Pharmacopoeia (USP)) or insurance company) of the level of sialylated glycans and/or value for one or more parameters listed in FIG. 3 (e.g., Glycan 1, Glycan 2, Glycan 3, or Glycan 4 listed in FIG. 3).

In certain other aspects, the disclosure provides methods of manufacturing ustekinumab drug product, such methods include a first step of providing (e.g., producing or expressing (e.g., in small scale or large scale cell culture) or manufacturing) or obtaining (e.g., receiving and/or purchasing from a third party (including a contractually related third party or a non-contractually-related (e.g., an independent) third party) a test glycoprotein preparation (e.g., a sample of a test glycoprotein preparation), a second step of acquiring (e.g., detecting, measuring, receiving, or obtaining, as discussed subsequently herein) a value for level of sialylated glycans for the test glycoprotein preparation, and a third step of processing at least a portion of the test glycoprotein preparation (e.g., processing a portion of a manufacturing lot, batch, or run, an entire manufacturing lot, batch, or run, or multiple manufacturing lots, batches, or runs) as ustekinumab drug product (e.g., in a form or packaging intended for marketing or administration as described subsequently herein) if the level of sialylated glycans is about 5%, 10%, 15%, 20%, 25% 30%, 35%, 40%, 50%, 10-20%, 20-30%, 30-40%, 40-50%, 10-50%, 20- 50%, 30-50%, 40-50%, or 25-35%; or a third step of taking an alternative action if the level of sialylated glycans is not about 5%, 10%, 15%, 20%, 25% 30%, 35%, 40%, 50%, 10-20%, 20-30%, 30-40%, 40-50%, 10-50%, 20-50%, 30-50%, 40-50%, or 25-35%.

In some instances, the second step includes acquiring at least one value (e.g., 1, 2, 3, or 4 values) for a ustekinumab parameter listed in FIG. 3 (e.g., Glycan 1, Glycan 2, Glycan 3, or Glycan 4 listed in FIG. 3) for the test glycoprotein preparation, and the third step includes processing at least a portion of the test glycoprotein preparation as ustekinumab drug product if the acquired value for parameter 1 (e.g., Glycan 1) is about 5-20% (e.g., about 5-10%, 10-20%, 7-12%, 5%, 6%, 7%, 8%, 9%, 10%, 11%, 12%, 13%, 14%, or 15%); the acquired value for parameter 2 (e.g., Glycan 2) is about 2-10% (e.g., about 2-5%, 5-10%, 3-7%, 2%, 3%, 4%, 5%, 6%, 7%, 8%, 9%, or 10%); the acquired value for parameter 3 (e.g., Glycan 3) is about 5-20% (e.g., about 5-10%, 10-20%, 7-12%, 5%, 6%, 7%, 8%, 9%, 10%, 11%, 12%, 13%, 14%, or 15%), and/or the acquired value for parameter 4 (e.g., Glycan 4) is about 0.5-5% (e.g., about 0.5-2.5%, 2.5-5%, 0.5%, 1%, 1.5%, 2%, or 2.5%), thereby manufacturing ustekinumab drug product.

In some instances, the second step includes acquiring at least one value (e.g., 1, 2, 3, or 4 values) for a ustekinumab parameter listed in FIG. 3 (e.g., Glycan 1, Glycan 2, Glycan 3, or Glycan 4 listed in FIG. 3) for the test glycoprotein preparation, and the third step includes processing at least a portion of the test glycoprotein preparation as ustekinumab drug product if at least one of the at least one value for the test glycoprotein preparation meets a reference criterion shown in FIG. 3 for the parameter, thereby manufacturing ustekinumab drug product. In some instances, the second step of such methods includes acquiring values for any combination of two or more ustekinumab parameters listed in FIG. 3 (e.g., Glycan 1, Glycan 2, Glycan 3, or Glycan 4 listed in FIG. 3), and the third step of such methods includes processing at least a portion of the test glycoprotein preparation as ustekinumab drug product if the values for the any combination of two or more ustekinumab parameters for the test glycoprotein preparation meet the corresponding reference criterion shown in FIG. 3 for the parameters. In some instances, the any combination of two or more ustekinumab parameters comprises: 2, 3, or 4 of the ustekinumab parameters listed in FIG. 3 (e.g., Glycan 1, Glycan 2, Glycan 3, or Glycan 4 listed in FIG. 3) and/or any two or more of parameter numbers 1, 2, 3, and/or 4 shown in FIG. 3. In some instances, the second step of such methods includes acquiring a value for a plurality of ustekinumab parameters listed in FIG. 3 (e.g., Glycan 1, Glycan 2, Glycan 3, or Glycan 4 listed in FIG. 3), and the third step of such methods includes processing at least a portion of the test glycoprotein preparation as ustekinumab drug product if the value for the plurality for the test glycoprotein preparation meets the corresponding reference criterion shown in FIG. 3 for the parameters. In some instances, the plurality of ustekinumab parameters includes 2, 3, or 4 of the ustekinumab parameters listed in FIG. 3 (e.g., Glycan 1, Glycan 2, Glycan 3, or Glycan 4 listed in FIG. 3).

In some instances, the test glycoprotein preparation obtained or produced in the first step of such methods includes a recombinant antibody composition having (i) a first amino acid sequence with at least 85% identity (e.g., about 90, 95, 98, or 100% identity) to SEQ ID NO:1 or a first amino acid sequence with at least 85% identity (e.g., about 90, 95, 98, or 100% identity) to SEQ ID NO:1 lacking 1, 2, 3, 4, or 5 amino acid residues at the amino and/or carboxyl terminus and (ii) a second amino acid sequence with at least 85% identity (e.g., about 90, 95, 98, or 100% identity) to SEQ ID NO:2 or a second amino acid sequence with at least 85% identity (e.g., about 90, 95, 98, or 100% identity) to SEQ ID NO:2 lacking 1, 2, 3, 4, or 5 amino acid residues at the amino and/or carboxyl terminus. In some instances, the recombinant antibody composition includes a first amino acid sequence with 100% identity to SEQ ID NO:1 (or to SEQ ID NO:1 lacking 1, 2, 3, 4, or 5 amino acid residues at the amino and/or carboxyl terminus) and a second amino acid sequence with 100% identity to SEQ ID NO:2 (or to SEQ ID NO:2 lacking 1, 2, 3, 4, or 5 amino acid residues at the amino and/or carboxyl terminus). In either instance, the first and second amino acid sequences combine when expressed to form the recombinant antibody in which the first sequence is the antibody heavy chain and the second sequence is the antibody light chain.

In some aspects, the disclosure provides methods of manufacturing ustekinumab drug product where such methods include a first step of providing (e.g., producing or expressing (e.g., in small scale or large scale cell culture) or manufacturing) or obtaining (e.g., receiving and/or purchasing from a third party (including a contractually related third party or a non-contractually-related (e.g., an independent) third party) a test glycoprotein preparation (e.g., a test glycoprotein drug substance, e.g., a sample of a test glycoprotein preparation or test glycoprotein drug substance), a second step of acquiring (e.g., detecting, measuring, receiving, or obtaining, as discussed subsequently herein) at least one value (e.g., 1, 2, 3, or 4 values) for a ustekinumab parameter listed in FIG. 3 (e.g., Glycan 1, Glycan 2, Glycan 3, or Glycan 4 listed in FIG. 3) for the test glycoprotein preparation, and a third step of processing at least a portion of the test glycoprotein preparation (e.g., processing a portion of a manufacturing lot, batch, or run, an entire manufacturing lot, batch, or run, or multiple manufacturing lots, batches, or runs) as ustekinumab drug product (e.g., in a form or packaging intended for marketing or administration as described subsequently herein) if the value for parameter 1 (e.g., Glycan 1) is about 5-20% (e.g., about 5-10%, 10-20%, 7-12%, 5%, 6%, 7%, 8%, 9%, 10%, 11%, 12%, 13%, 14%, or 15%); the value for parameter 2 (e.g., Glycan 2) is about 2-10% (e.g., about 2-5%, 5-10%, 3-7%, 2%, 3%, 4%, 5%, 6%, 7%, 8%, 9%, or 10%); the value for parameter 3 (e.g., Glycan 3) is about 5-20% (e.g., about 5-10%, 10-20%, 7-12%, 5%, 6%, 7%, 8%, 9%, 10%, 11%, 12%, 13%, 14%, or 15%), and the value for parameter 4 (e.g., Glycan 4) is about 0.5-5% (e.g., about 0.5-2.5%, 2.5-5%, 0.5%, 1%, 1.5%, 2%, or 2.5%); or a third step of taking an alternative action if the value for parameter 1 (e.g., Glycan 1) is not about 5-20% (e.g., about 5-10%, 10-20%, 7-12%, 5%, 6%, 7%, 8%, 9%, 10%, 11%, 12%, 13%, 14%, or 15%); the value for parameter 2 (e.g., Glycan 2) is not about 2-10% (e.g., about 2-5%, 5-10%, 3-7%, 2%, 3%, 4%, 5%, 6%, 7%, 8%, 9%, or 10%); the value for parameter 3 (e.g., Glycan 3) is not about 5-20% (e.g., about 5-10%, 10-20%, 7-12%, 5%, 6%, 7%, 8%, 9%, 10%, 11%, 12%, 13%, 14%, or 15%), and/or the value for parameter 4 (e.g., Glycan 4) is not about 0.5-5% (e.g., about 0.5-2.5%, 2.5-5%, 0.5%, 1%, 1.5%, 2%, or 2.5%).

In some embodiments, the alternative action comprises one or more of disposing of the test glycoprotein preparation (e.g., test protein drug substance), classifying for disposal the test glycoprotein preparation (e.g., test protein drug substance), labeling the test glycoprotein preparation (e.g., test protein drug substance) for disposal, and reprocessing the test glycoprotein preparation (e.g., test protein drug substance).

In some aspects, the disclosure provides methods of manufacturing ustekinumab drug product where such methods include a first step of providing (e.g., producing or expressing (e.g., in small scale or large scale cell culture) or manufacturing) or obtaining (e.g., receiving and/or purchasing from a third party (including a contractually related third party or a non-contractually-related (e.g., an independent) third party) a test glycoprotein preparation (e.g., a test glycoprotein drug substance, e.g., a sample of a test glycoprotein preparation or test glycoprotein drug substance), a second step of acquiring (e.g., detecting, measuring, receiving, or obtaining, as discussed subsequently herein) at least one value (e.g., 1, 2, 3, or 4 values) for a ustekinumab parameter listed in FIG. 3 (e.g., Glycan 1, Glycan 2, Glycan 3, or Glycan 4 listed in FIG. 3) for the test glycoprotein preparation, and a third step of processing at least a portion of the test glycoprotein preparation (e.g., processing a portion of a manufacturing lot, batch, or run, an entire manufacturing lot, batch, or run, or multiple manufacturing lots, batches, or runs) as ustekinumab drug product (e.g., in a form or packaging intended for marketing or administration as described subsequently herein) if the value for each parameter listed in FIG. 3 for the test glycoprotein preparation meets the reference criterion shown in FIG. 3; or a third step of taking an alternative action if the value for one or more parameters listed in FIG. 3 for the test glycoprotein preparation does not meet the reference criterion shown in FIG. 3.

In some embodiments, the alternative action comprises one or more of disposing of the test glycoprotein preparation (e.g., test protein drug substance), classifying for disposal the test glycoprotein preparation (e.g., test protein drug substance), labeling the test glycoprotein preparation (e.g., test protein drug substance) for disposal, and reprocessing the test glycoprotein preparation (e.g., test protein drug substance).

In some instances, the test glycoprotein obtained or produced in the first step of such methods includes a recombinant antibody composition having (i) a first amino acid sequence with at least 85% identity (e.g., about 90, 95, 98, or 100% identity) to SEQ ID NO:1 or a first amino acid sequence with at least 85% identity (e.g., about 90, 95, 98, or 100% identity) to SEQ ID NO:1 lacking 1, 2, 3, 4, or 5 amino acid residues at the amino and/or carboxyl terminus and (ii) a second amino acid sequence with at least 85% identity (e.g., about 90, 95, 98, or 100% identity) to SEQ ID NO:2 or a second amino acid sequence with at least 85% identity (e.g., about 90, 95, 98, or 100% identity) to SEQ ID NO:2 lacking 1, 2, 3, 4, or 5 amino acid residues at the amino and/or carboxyl terminus. In some instances, the recombinant antibody composition includes a first amino acid sequence with 100% identity to SEQ ID NO:1 (or to SEQ ID NO:1 lacking 1, 2, 3, 4, or 5 amino acid residues at the amino and/or carboxyl terminus) and a second amino acid sequence with 100% identity to SEQ ID NO:2 (or to SEQ ID NO:2 lacking 1, 2, 3, 4, or 5 amino acid residues at the amino and/or carboxyl terminus). In either instance, the first and second amino acid sequences combine when expressed to form the recombinant antibody in which the first sequence is the antibody heavy chain and the second sequence is the antibody light chain.

In another aspect, the disclosure provides methods of manufacturing ustekinumab drug product in which such methods include providing a host cell that is genetically engineered to express (i) a first amino acid sequence having a sequence with at least about 85% identity (e.g., about 90, 95, 98, or 100% identity) to SEQ ID NO:1 or to SEQ ID NO:1 lacking 1, 2, 3, 4, or 5 amino acid residues at the amino and/or carboxyl terminus and (ii) a second amino acid sequence having a sequence with at least about 85% identity (e.g., about 90, 95, 98, or 100% identity) to SEQ ID NO:2 or to SEQ ID NO:2 lacking 1, 2, 3, 4, or 5 amino acid residues at the amino and/or carboxyl terminus; culturing the host cell under conditions whereby the cell expresses the first and second amino acid sequences, wherein the expressed first and second amino acid sequences form recombinant antibodies; harvesting (e.g., isolating and/or purifying) recombinant antibodies from the host cell culture to produce an antibody preparation; acquiring (e.g., detecting, measuring, receiving, or obtaining, as discussed subsequently herein) a value for level of sialylated glycans for the antibody preparation; and (i) processing at least a portion of the antibody preparation (e.g., processing a portion of a manufacturing lot, batch, or run, an entire manufacturing lot, batch, or run, or multiple manufacturing lots, batches, or runs) into ustekinumab drug product (e.g., in a form or packaging intended for marketing or administration as described subsequently herein) if the value for level of sialylated glycans is about 5%, 10%, 15%, 20%, 25% 30%, 35%, 40%, 50%, 10-20%, 20-30%, 30-40%, 40-50%, 10-50%, 20-50%, 30-50%, 40-50%, or 25-35%; or (ii) taking alternative action if the value for level of sialylated glycans is not about 5%, 10%, 15%, 20%, 25% 30%, 35%, 40%, 50%, 10-20%, 20-30%, 30-40%, 40-50%, 10-50%, 20-50%, 30-50%, 40-50%, or 25-35%.

In some embodiments, the alternative action comprises one or more of disposing of the antibody preparation (e.g., batch of the antibody preparation), classifying for disposal the antibody preparation (e.g., batch of the antibody preparation), labeling the antibody preparation (e.g., batch of the antibody preparation) for disposal, and reprocessing the antibody preparation (e.g., batch of the antibody preparation).

In some instances, the method includes acquiring a value for each parameter listed in FIG. 3 (e.g., Glycan 1, Glycan 2, Glycan 3, or Glycan 4 listed in FIG. 3) for the antibody preparation, and processing at least a portion of the antibody preparation into ustekinumab drug product if the value for parameter 1 (e.g., Glycan 1) is about 5-20% (e.g., about 5-10%, 10-20%, 7-12%, 5%, 6%, 7%, 8%, 9%, 10%, 11%, 12%, 13%, 14%, or 15%); the value for parameter 2 (e.g., Glycan 2) is about 2-10% (e.g., about 2-5%, 5-10%, 3-7%, 2%, 3%, 4%, 5%, 6%, 7%, 8%, 9%, or 10%); the value for parameter 3 (e.g., Glycan 3) is about 5-20% (e.g., about 5-10%, 10-20%, 7-12%, 5%, 6%, 7%, 8%, 9%, 10%, 11%, 12%, 13%, 14%, or 15%), and the value for parameter 4 (e.g., Glycan 4) is about 0.5-5% (e.g., about 0.5-2.5%, 2.5-5%, 0.5%, 1%, 1.5%, 2%, or 2.5%), thereby manufacturing ustekinumab drug product.

In some instances, the method includes acquiring a value for each parameter listed in FIG. 3 (e.g., Glycan 1, Glycan 2, Glycan 3, or Glycan 4 listed in FIG. 3) for the antibody preparation, and processing at least a portion of the antibody preparation into ustekinumab drug product if the value for each parameter listed in FIG. 3 for the antibody preparation meets the reference criterion shown in FIG. 3, thereby manufacturing ustekinumab drug product.

In a further aspect, the disclosure provides methods of manufacturing ustekinumab drug product in which such methods include providing a host cell that is genetically engineered to express (i) a first amino acid sequence having a sequence with at least 85% identity (e.g., about 90, 95, 98, or 100% identity) to SEQ ID NO:1 or to SEQ ID NO:1 lacking 1, 2, 3, 4, or 5 amino acid residues at the amino and/or carboxyl terminus and (ii) a second amino acid sequence having a sequence with at least 85% identity (e.g., about 90, 95, 98, or 100% identity) to SEQ ID NO:2 or to SEQ ID NO:2 lacking 1, 2, 3, 4, or 5 amino acid residues at the amino and/or carboxyl terminus; culturing the host cell under conditions whereby the cell expresses the first and second amino acid sequences, wherein the expressed first and second amino acid sequences form recombinant antibodies, harvesting (e.g., isolating and/or purifying) recombinant antibodies from the host cell culture to produce an antibody preparation, acquiring (e.g., detecting, measuring, receiving, or obtaining, as discussed subsequently herein) at least one value (e.g., 1, 2, 3, or 4 values) for a ustekinumab parameter listed in FIG. 3 (e.g., Glycan 1, Glycan 2, Glycan 3, or Glycan 4 listed in FIG. 3) for the antibody preparation; and (i) processing or directing the processing of at least a portion of the antibody preparation (e.g., processing a portion of a manufacturing lot, batch, or run, an entire manufacturing lot, batch, or run, or multiple manufacturing lots, batches, or runs) into ustekinumab drug product (e.g., in a form or packaging intended for marketing or administration as described subsequently herein) if the acquired value for parameter 1 (e.g., Glycan 1) is about 5-20% (e.g., about 5-10%, 10-20%, 7-12%, 5%, 6%, 7%, 8%, 9%, 10%, 11%, 12%, 13%, 14%, or 15%); the acquired value for parameter 2 (e.g., Glycan 2) is about 2-10% (e.g., about 2-5%, 5-10%, 3-7%, 2%, 3%, 4%, 5%, 6%, 7%, 8%, 9%, or 10%); the acquired value for parameter 3 (e.g., Glycan 3) is about 5-20% (e.g., about 5-10%, 10-20%, 7-12%, 5%, 6%, 7%, 8%, 9%, 10%, 11%, 12%, 13%, 14%, or 15%), and/or the acquired value for parameter 4 (e.g., Glycan 4) is about 0.5-5% (e.g., about 0.5-2.5%, 2.5-5%, 0.5%, 1%, 1.5%, 2%, or 2.5%); or (ii) taking alternative action if the acquired value for parameter 1 (e.g., Glycan 1) is not about 5-20% (e.g., about 5-10%, 10-20%, 7-12%, 5%, 6%, 7%, 8%, 9%, 10%, 11%, 12%, 13%, 14%, or 15%); the acquired value for parameter 2 (e.g., Glycan 2) is not about 2-10% (e.g., about 2-5%, 5-10%, 3-7%, 2%, 3%, 4%, 5%, 6%, 7%, 8%, 9%, or 10%); the acquired value for parameter 3 (e.g., Glycan 3) is not about 5-20% (e.g., about 5-10%, 10-20%, 7-12%, 5%, 6%, 7%, 8%, 9%, 10%, 11%, 12%, 13%, 14%, or 15%), and/or the acquired value for parameter 4 (e.g., Glycan 4) is not about 0.5-5% (e.g., about 0.5-2.5%, 2.5-5%, 0.5%, 1%, 1.5%, 2%, or 2.5%).

In some embodiments, the alternative action comprises one or more of disposing of the antibody preparation (e.g., batch of the antibody preparation), classifying for disposal the antibody preparation (e.g., batch of the antibody preparation), labeling the antibody preparation (e.g., batch of the antibody preparation) for disposal, and reprocessing the antibody preparation (e.g., batch of the antibody preparation).

In some instances, the method includes processing at least a portion of the antibody preparation into ustekinumab drug product if at least one of the at least one value for the antibody preparation meets a reference criterion shown in FIG. 3 (e.g., Glycan 1, Glycan 2, Glycan 3, or Glycan 4 listed in FIG. 3), thereby manufacturing ustekinumab drug product. In some instances, such methods include acquiring values for any combination of two or more ustekinumab parameters listed in FIG. 3 (e.g., Glycan 1, Glycan 2, Glycan 3, or Glycan 4 listed in FIG. 3), and processing at least a portion of the test glycoprotein preparation as ustekinumab drug product if the values for the any combination of two or more ustekinumab parameters for the test glycoprotein preparation meet the corresponding reference criterion shown in FIG. 3 for the parameters. In some instances, the any combination of two or more ustekinumab parameters comprises: 2, 3, or 4 of the ustekinumab parameters listed in FIG. 3 (e.g., Glycan 1, Glycan 2, Glycan 3, or Glycan 4 listed in FIG. 3) and/or any two or more of parameter numbers 1, 2, 3, and/or 4 shown in FIG. 3. In some embodiments, such methods include acquiring a value for a plurality of ustekinumab parameters listed in FIG. 3 (e.g., Glycan 1, Glycan 2, Glycan 3, or Glycan 4 listed in FIG. 3), and processing at least a portion of the test glycoprotein preparation as ustekinumab drug product if the value for the plurality for the test glycoprotein preparation meets the corresponding reference criterion shown in FIG. 3 for the parameters. In some instances, the plurality includes 2, 3, or 4 of the ustekinumab parameters listed in FIG. 3 (e.g., Glycan 1, Glycan 2, Glycan 3, or Glycan 4 listed in FIG. 3), and/or any two or more of parameter numbers 1, 2, 3, or 4 shown in FIG. 3.

In some embodiments, methods herein can include, after the (second) step of acquiring the value(s) and before the (third) step of processing, a further step of obtaining a plurality of assessments made by comparing the value(s) with a corresponding reference criterion (e.g., shown in FIG. 3).

In some embodiments, methods herein include directly obtaining at least one value by performing an analytical test on the test glycoprotein preparation or antibody preparation. For example, such values can be directly obtained using a method provided in Table 1.

In some embodiments, the processing step encompassed by the methods herein includes combining the test glycoprotein or antibody preparation with an excipient or buffer. In some embodiments, the processing step encompassed by the methods herein includes, but is not limited to, one or more of: formulating the test glycoprotein preparation or antibody preparation; processing the test glycoprotein preparation or antibody preparation into a drug product; combining the test glycoprotein preparation or antibody preparation with a second component, e.g., an excipient or buffer; changing the concentration of the test glycoprotein or antibody in the preparation; lyophilizing the test glycoprotein preparation or antibody preparation; combining a first and second aliquot of the test glycoprotein preparation or antibody preparation to provide a third, larger, aliquot; dividing the test glycoprotein preparation or antibody preparation into smaller aliquots; disposing the test glycoprotein preparation or antibody preparation into a container, e.g., a gas or liquid tight container; packaging the test glycoprotein preparation or antibody preparation; associating a container comprising the test glycoprotein preparation or antibody preparation with a label (e.g., labeling); shipping or moving the test glycoprotein preparation or antibody preparation to a different location.

In some embodiments, the processed drug product or antibody is approved under Section 351(k) of the Public Health Service (PHS) Act. In some embodiments, the processed drug product or antibody is not approved under biologics license application (BLA) under Section 351(a) of the Public Health Service (PHS) Act.

In some embodiments, the reference criteria shown in FIG. 3 are acquired from ustekinumab approved under a biologics license application (BLA) under Section 351(a) of the Public Health Service (PHS) Act.

In some embodiments, the value for the test glycoprotein preparation (e.g., the obtained value for level of sialylated glycans and/or obtained value to be compared with FIG. 3) comprises an average (e.g., mean) of a range of values for the parameter for multiple (e.g., 2, 3, 4, 5, 10, 15, 20, or more) batches or samples of the test glycoprotein preparation or antibody preparation.

In some embodiments, one or more, including all, of the reference criterion shown in FIG. 3 is/are a specification for commercial release of a drug product under Section 351(k) of the Public Health Service (PHS) Act.

In some embodiments, the value for the test glycoprotein preparation is acquired for one, two, or more samples or batches of the test glycoprotein preparation, e.g., to facilitate calculation of an average value.

In some instances, evaluation methods include, for a glycoprotein preparation, evaluating information (e.g., value(s)) pertaining to one or more ustekinumab-specific parameters and, optionally, providing, e.g., acquiring, a determination of whether the information meets a ustekinumab signature, e.g., by comparing the information with the ustekinumab signature and/or confirming that the information has a defined (e.g., predefined) relationship with the ustekinumab signature.

In some instances, evaluation methods include, for a glycoprotein preparation, evaluating information (e.g., value(s)) pertaining to level of sialylated glycans and/or one or more of the ustekinumab parameters disclosed in FIG. 3 (e.g., Glycan 1, Glycan 2, Glycan 3, or Glycan 4 listed in FIG. 3), and, optionally, providing, e.g., acquiring, a determination of whether the information meets a ustekinumab signature, e.g., by comparing the information with the ustekinumab signature and/or confirming that the information has a defined (e.g., predefined) relationship with the ustekinumab signature. For example, for a given glycoprotein preparation, methods can include: evaluating level of sialylated glycans and obtaining a value therefor, and, optionally, determining whether the value is about 5%, 10%, 15%, 20%, 25% 30%, 35%, 40%, 50%, 10-20%, 20-30%, 30-40%, 40-50%, 10-50%, 20-50%, 30-50%, 40-50%, or 25-35%, wherein, in this example, the value for level of sialylated glycans would conform to the ustekinumab signature if it is about 5%, 10%, 15%, 20%, 25% 30%, 35%, 40%, 50%, 10-20%, 20-30%, 30-40%, 40-50%, 10-50%, 20-50%, 30-50%, 40-50%, or 25-35% In another example, for a given glycoprotein preparation, methods can include:

evaluating parameter 1 (e.g., Glycan 1) and obtaining a value therefor, and, optionally, determining whether the value conforms to the reference criterion for parameter 1 (e.g., Glycan 1) provided in FIG. 3, wherein, in this example, the reference criterion for parameter 1 (e.g., Glycan 1) is a ustekinumab signature. In this instance, the value for parameter 1 (e.g., Glycan 1) would conform to the ustekinumab signature if it is greater than 6%. In another example, for a given glycoprotein preparation, methods can include: evaluating parameter 2 (e.g., Glycan 2) and obtaining a value therefor, and, optionally, determining whether the value conforms to the reference criterion for parameter 2 (e.g., Glycan 2) provided in FIG. 3, wherein, in this example, the reference criterion for parameter 2 is a ustekinumab signature. In this instance, the value for parameter 2 (e.g., Glycan 2) would conform to the ustekinumab signature if it is greater than 3%. In another example, for a given glycoprotein preparation, methods can include: evaluating parameter 3 (e.g., Glycan 3) and obtaining a value therefor, and, optionally, determining whether the value conforms to the reference criterion for parameter 3 (e.g., Glycan 3) provided in FIG. 3, wherein, in this example, the reference criterion for parameter 3 is a ustekinumab signature. In this instance, the value for parameter 3 (e.g., Glycan 3) would conform to the ustekinumab signature if it is greater than 7%. In another example, for a given glycoprotein preparation, methods can include: evaluating parameter 4 (e.g., Glycan 4) and obtaining a value therefor, and, optionally, determining whether the value conforms to the reference criterion for parameter 4 provided in FIG. 3, wherein, in this example, the reference criterion for parameter 4 is a ustekinumab signature. In this instance, the value for parameter 4 (e.g., Glycan 4) would conform to the ustekinumab signature if it is greater than 0.5%.

In another aspect, the disclosure provides methods of identifying a test glycoprotein preparation (e.g., such as a glycoprotein drug substance or drug product preparation) as ustekinumab. In some instances, identification methods include, for a glycoprotein preparation, evaluating information (e.g., value(s)) pertaining to level of sialylated glycans and/or one or more ustekinumab-specific parameters, providing, e.g., acquiring, a determination of whether the information meets a ustekinumab signature, e.g., by comparing the information with the ustekinumab signature and/or confirming that the information has a defined (e.g., predefined) relationship with the ustekinumab signature, and identifying the glycoprotein preparation as ustekinumab if the information meets the ustekinumab signature.

In some instances, identification methods include, for a glycoprotein preparation, evaluating information (e.g., value(s)) pertaining to level of sialylated glycans and/or one or more of the ustekinumab parameters disclosed in FIG. 3 (e.g., Glycan 1, Glycan 2, Glycan 3, or Glycan 4 listed in FIG. 3), providing, e.g., acquiring, a determination of whether the information meets a ustekinumab signature, e.g., by comparing the information with the ustekinumab signature and/or confirming that the information has a defined (e.g., predefined) relationship with the ustekinumab signature, and identifying the glycoprotein preparation as ustekinumab if the acquired information meets the ustekinumab signature.

For example, for a given glycoprotein preparation, methods can include: evaluating level of sialylated glycans and obtaining a value therefor, determining whether the value is about 5%, 10%, 15%, 20%, 25% 30%, 35%, 40%, 50%, 10-20%, 20-30%, 30-40%, 40-50%, 10-50%, 20-50%, 30-50%, 40-50%, or 25-35%, and identifying the glycoprotein preparation as ustekinumab if the information conforms, wherein, in this example, the level of sialylated glycans of about 5%, 10%, 15%, 20%, 25% 30%, 35%, 40%, 50%, 10-20%, 20-30%, 30-40%, 40-50%, 10-50%, 20-50%, 30-50%, 40-50%, or 25-35% is a ustekinumab signature. In another example, for a given glycoprotein preparation, methods can include: evaluating parameter 1 (e.g., Glycan 1) and obtaining a value therefor, determining whether the value conforms to the reference criterion for parameter 1 (e.g., Glycan 1) provided in FIG. 3, and identifying the glycoprotein preparation as ustekinumab if the information conforms, wherein, in this example, the reference criterion for parameter 1 is a ustekinumab signature. In this instance, the value for parameter 1 (e.g., Glycan 1) would conform to the ustekinumab signature if it is greater than 6%. In another example, for a given glycoprotein preparation, methods can include: evaluating parameter 2 (e.g., Glycan 2) and obtaining a value therefor, and, optionally, determining whether the value conforms to the reference criterion for parameter 2 (e.g., Glycan 2) provided in FIG. 3, wherein, in this example, the reference criterion for parameter 2 is a ustekinumab signature. In this instance, the value for parameter 2 (e.g., Glycan 2) would conform to the ustekinumab signature if it is greater than 3%. In another example, for a given glycoprotein preparation, methods can include: evaluating parameter 3 (e.g., Glycan 3) and obtaining a value therefor, and, optionally, determining whether the value conforms to the reference criterion for parameter 3 (e.g., Glycan 3) provided in FIG. 3, wherein, in this example, the reference criterion for parameter 3 is a ustekinumab signature. In this instance, the value for parameter 3 (e.g., Glycan 3) would conform to the ustekinumab signature if it is greater than 7%. In another example, for a given glycoprotein preparation, methods can include: evaluating parameter 4 (e.g., Glycan 4) and obtaining a value therefor, and, optionally, determining whether the value conforms to the reference criterion for parameter 4 (e.g., Glycan 4) provided in FIG. 3, wherein, in this example, the reference criterion for parameter 4 is a ustekinumab signature. In this instance, the value for parameter 4 (e.g., Glycan 4) would conform to the ustekinumab signature if it is greater than 0.5%.

In a further aspect, the disclosure provides methods of producing (e.g., manufacturing) ustekinumab (e.g., ustekinumab drug product). In some instances, production methods include, for a glycoprotein preparation, evaluating information (e.g., value(s)) pertaining to level of sialylated glycans and/or one or more ustekinumab-specific parameters, providing, e.g., acquiring, a determination of whether the information meets a ustekinumab signature, e.g., by comparing the information with the ustekinumab signature and/or confirming that the information has a defined (e.g., predefined) relationship with the ustekinumab signature, and (i) processing the glycoprotein preparation (e.g., as ustekinumab drug product) if the information meets the ustekinumab signature, or (ii) taking an alternative action if the information does not meet the ustekinumab signature.

In some embodiments, the alternative action comprises one or more of disposing of the glycoprotein preparation (e.g., batch of the glycoprotein preparation), classifying for disposal the glycoprotein preparation (e.g., batch of the glycoprotein preparation), labeling the glycoprotein preparation (e.g., batch of the glycoprotein preparation) for disposal, and reprocessing the glycoprotein preparation (e.g., batch of the glycoprotein preparation).

In some instances, production methods include, for a glycoprotein preparation, evaluating information (e.g., value(s)) pertaining to level of sialylated glycans and/or one or more ustekinumab parameters disclosed in FIG. 3 (e.g., Glycan 1, Glycan 2, Glycan 3, or Glycan 4 listed in FIG. 3), providing, e.g., acquiring, a determination of whether the information meets a ustekinumab signature, e.g., by comparing the information with the ustekinumab signature and/or confirming that the information has a defined (e.g., predefined) relationship with the ustekinumab signature, and (i) processing the glycoprotein preparation (e.g., as ustekinumab drug product) if the information meets the ustekinumab signature, or (ii) taking alternative action if the information does not meet the ustekinumab signature. For example, for a given glycoprotein preparation, production methods can include: evaluating a value for level of sialylated glycans for the glycoprotein preparation, and (i) processing the glycoprotein preparation as ustekinumab drug product if the value obtained is about 5%, 10%, 15%, 20%, 25% 30%, 35%, 40%, 50%, 10-20%, 20-30%, 30-40%, 40-50%, 10-50%, 20-50%, 30-50%, 40-50%, or 25-35%, or (ii) taking alternative action if the value obtained is not about 5%, 10%, 15%, 20%, 25% 30%, 35%, 40%, 50%, 10-20%, 20-30%, 30-40%, 40-50%, 10-50%, 20-50%, 30-50%, 40-50%, or 25-35%. In another example, for a given glycoprotein preparation, production methods can include: evaluating a value for parameter 1 (e.g., Glycan 1) for the glycoprotein preparation, comparing the value with the reference criterion for parameter 1 (e.g., Glycan 1) provided in FIG. 3, determining whether the value obtained meets with the reference value for parameter 1, and (i) processing the glycoprotein preparation as ustekinumab drug product if the value obtained meets the reference criterion for parameter 1, wherein, in this example, the reference criterion for parameter 1 (e.g., Glycan 1) is a ustekinumab signature, or (ii) taking alternative action if the value obtained does not meet the reference criterion for parameter 1. In this instance, the value for parameter 1 (e.g., Glycan 1) would conform to the reference criterion for parameter 1 (e.g., Glycan 1) if it is greater than 6%. In another example, for a given glycoprotein preparation, production methods can include: evaluating a value for parameter 2 (e.g., Glycan 2) for the glycoprotein preparation, comparing the value with the reference criterion for parameter 2 (e.g., Glycan 2) provided in FIG. 3, determining whether the value obtained meets with the reference value for parameter 2, and (i) processing the glycoprotein preparation as ustekinumab drug product if the value obtained meets the reference criterion for parameter 2, wherein, in this example, the reference criterion for parameter 2 (e.g., Glycan 2) is a ustekinumab signature, or (ii) taking alternative action if the value obtained does not meet the reference criterion for parameter 2. In this instance, the value for parameter 2 (e.g., Glycan 2) would conform to the reference criterion for parameter 2 (e.g., Glycan 2) if it is greater than 3%. In another example, for a given glycoprotein preparation, production methods can include: evaluating a value for parameter 3 (e.g., Glycan 3) for the glycoprotein preparation, comparing the value with the reference criterion for parameter 3 (e.g., Glycan 3) provided in FIG. 3, determining whether the value obtained meets with the reference value for parameter 3, and (i) processing the glycoprotein preparation as ustekinumab drug product if the value obtained meets the reference criterion for parameter 3, wherein, in this example, the reference criterion for parameter 3 (e.g., Glycan 3) is a ustekinumab signature, or (ii) taking an alternative action if the value obtained does not meet the reference criterion for parameter 3. In this instance, the value for parameter 3 (e.g., Glycan 3) would conform to the reference criterion for parameter 3 (e.g., Glycan 3) if it is greater than 7%. In another example, for a given glycoprotein preparation, production methods can include: evaluating a value for parameter 4 (e.g., Glycan 4) for the glycoprotein preparation, comparing the value with the reference criterion for parameter 4 (e.g., Glycan 4) provided in FIG. 3, determining whether the value obtained meets with the reference value for parameter 4, and (i) processing the glycoprotein preparation as ustekinumab drug product if the value obtained meets the reference criterion for parameter 4, wherein, in this example, the reference criterion for parameter 4 (e.g., Glycan 4) is a ustekinumab signature, or (ii) taking an alternative action if the value obtained does not meet the reference criterion for parameter 4. In this instance, the value for parameter 4 (e.g., Glycan 4) would conform to the reference criterion for parameter 4 (e.g., Glycan 4) if it is greater than 0.5%. In some instances, these methods can further include packaging, labeling, and/or shipping the ustekinumab drug product, e.g., as discussed in further detail herein.

In some embodiments, the alternative action comprises one or more of disposing of the glycoprotein preparation (e.g., batch of the glycoprotein preparation), classifying for disposal the glycoprotein preparation (e.g., batch of the glycoprotein preparation), labeling the glycoprotein preparation (e.g., batch of the glycoprotein preparation) for disposal, and reprocessing the glycoprotein preparation (e.g., batch of the glycoprotein preparation).

As used herein, a ustekinumab signature comprises a plurality of reference criteria or rules for a plurality of parameters that define ustekinumab. In some instances, a ustekinumab signature can be a pharmaceutical specification, a commercial product release specification, a product acceptance criterion, a pharmacopeial standard, or a product labeling description. In some instances, the ustekinumab signature comprises a level of sialylated glycans of about 5%, 10%, 15%, 20%, 25% 30%, 35%, 40%, 50%, 10-20%, 20-30%, 30-40%, 40-50%, 10-50%, 20- 50%, 30-50%, 40-50%, or 25-35%. In some instances, the ustekinumab signature comprises a plurality of reference criteria or rules for a plurality of parameters shown in FIG. 3.

In some instances, the ustekinumab signature comprises a value for parameter 1 of FIG. 3 of about 5-20% (e.g., about 5-10%, 10-20%, 7-12%, 5%, 6%, 7%, 8%, 9%, 10%, 11%, 12%, 13%, 14%, or 15%); a value for parameter 2 of FIG. 3 of about 2-10% (e.g., about 2-5%, 5-10%, 3-7%, 2%, 3%, 4%, 5%, 6%, 7%, 8%, 9%, or 10%); a value for parameter 3 of FIG. 3 of about 5-20% (e.g., about 5-10%, 10-20%, 7-12%, 5%, 6%, 7%, 8%, 9%, 10%, 11%, 12%, 13%, 14%, or 15%), and/or a value for parameter 4 of FIG. 3 of about 0.5-5% (e.g., about 0.5-2.5%, 2.5-5%, 0.5%, 1%, 1.5%, 2%, or 2.5%).

While the present disclosure provides exemplary units and methods for the evaluation, identification, and production methods disclosed herein (see, e.g., Tables 1 and 2), a person of ordinary skill in the art will appreciate that performance of the evaluation, identification, and production methods herein is not limited to use of those units and/or methods. For example, ustekinumab signatures provided herein are generally described, for each parameter, as a value for a glycan or structure relative to total glycan on a mol/mol basis (see, e.g., FIG. 3). A person of skill in the art understands that although the use of other metrics or units (e.g., mass/mass, mole percent vs. weight percent) to measure a described parameter might give rise to different absolute values than those described herein, e.g., in FIG. 3, a test glycoprotein preparation meets a disclosed ustekinumab reference criterion or signature even if other units or metrics are used, as long as the test glycoprotein preparation meets the herein disclosed reference criterion or signature when the herein disclosed units and metrics are used, e.g., allowing for the sensitivity (e.g., analytical variability) of the method being used to measure the value.

Ustekinumab parameters shown in FIG. 3 are parameters that, alone, in any combination, or together, distinguish ustekinumab from non-ustekinumab glycoprotein (see below). In some instances, a ustekinumab parameter is part of the glycoprotein, e.g., connected with the rest of the glycoprotein by a covalent bond, i.e., an intrinsic parameter. Intrinsic parameters include the presence, absence, level, ratio (with another entity), or distribution of a physical moiety, e.g., a moiety arising from or associated with a post-translational event. Exemplary parameters include the presence (or absence), abundance, absolute or relative amount, ratio (with another entity), or distribution of a glycan, a linkage, a glycoform, or post-translationally added components of the preparation. In some instances, a parameter is not part of the glycoprotein but is present in the preparation with the glycoprotein (i.e., in a glycoprotein preparation), i.e., an extrinsic, parameter. Exemplary parameters of this type include the presence (or absence), abundance, ratio (with another entity), or distribution of, e.g., impurities, e.g., host cell proteins, residue from purification processes, viral impurities, and enclosure components.

In some instances, a ustekinumab signature comprises reference criteria or rules for 2, 3, 4 or substantially all, parameters shown in FIG. 3. In some instances, a ustekinumab signature comprises reference criteria or rules for two or more (e.g., 2, 3, or 4) of ustekinumab parameter(s) 1, 2, 3, and/or 4. In some instances, a ustekinumab signature comprises predetermined reference criteria or rule(s) for 2, 3, or 4 parameters shown in FIG. 3.

In some instances, methods (i.e., evaluation, identification, and production methods) can further include, e.g., one or more of: providing or obtaining a glycoprotein preparation (e.g., such as a glycoprotein drug substance or a precursor thereof); memorializing confirmation or identification of the glycoprotein preparation as ustekinumab using a recordable medium (e.g., on paper or in a computer readable medium, e.g., in a Certificate of Testing, Certificate of Analysis, Material Safety Data Sheet (MSDS), batch record, or Certificate of Analysis (CofA)); informing a party or entity (e.g., a contractual or manufacturing partner, a care giver or other end-user, a regulatory entity, e.g., the FDA or other U.S., European, Japanese, Chinese or other governmental agency, or another entity, e.g., a compendial entity (e.g., U.S. Pharmacopoeia (USP)) or insurance company) that a glycoprotein preparation is ustekinumab; selecting the glycoprotein preparation for further processing (e.g., processing (e.g., formulating) the glycoprotein preparation as a drug product (e.g., a pharmaceutical product) if the glycoprotein preparation is identified as ustekinumab; reprocessing or disposing of the glycoprotein preparation if the glycoprotein preparation is not identified as ustekinumab.

In some instances, methods (i.e., evaluation, identification, and production methods) include taking action (e.g., physical action) in response to the methods disclosed herein. For example, the glycoprotein preparation is classified, selected, accepted or discarded, released or withheld, processed into a drug product, shipped, moved to a different location, formulated, labeled, packaged, released into commerce, or sold or offered for sale, depending on whether the preselected relationship is met.

In some instances, processing may include formulating, packaging (e.g., in a syringe or vial), labeling, or shipping at least a portion of the glycoprotein preparation. In some instances, processing includes formulating, packaging (e.g., in a syringe or vial), and labeling at least a portion of the glycoprotein as ustekinumab drug product. Processing can include directing and/or contracting another party to process as described herein.

Definitions

As used herein, a "glycoprotein" refers to amino acid sequences that include one or more oligosaccharide chains (e.g., glycans) covalently attached thereto. Exemplary amino acid sequences include peptides, polypeptides and proteins. Exemplary glycoproteins include glycosylated antibodies and antibody-like molecules (e.g., Fc fusion proteins). Exemplary antibodies include monoclonal antibodies and/or fragments thereof, polyclonal antibodies and/or fragments thereof, and Fc domain containing fusion proteins (e.g., fusion proteins containing the Fc region of IgG1, or a glycosylated portion thereof). A "glycoprotein preparation" is a composition or mixture that includes at least one glycoprotein.

A glycoprotein preparation (e.g., such as a glycoprotein drug substance or a precursor thereof) included herein is or includes a glycoprotein (e.g., an antibody) that has a first amino acid sequence with at least 85% identity to SEQ ID NO:1 (or to SEQ ID NO:1 lacking 1-5 amino acid residues at the amino and/or carboxyl terminus) and a second amino acid sequence with at least 85% identity to SEQ ID NO:2 (or to SEQ ID NO:2 lacking 1-5 amino acid residues at the amino and/or carboxyl terminus). In some instances, the first and/or second amino acid sequence(s) have at least 90%, 91%, 92%, 93%, 94%, 95%, 96%, 97%, 98%, 99%, or 100% identity to SEQ ID NO:1 and/or at least 90%, 91%, 92%, 93%, 94%, 95%, 96%, 97%, 98%, 99%, or 100% identity to SEQ ID NO:2.

In some instances, a glycoprotein preparation (e.g., such as a glycoprotein drug substance or a precursor thereof) can be a sample from a proposed or test batch of ustekinumab drug substance or drug product. As used herein, a "batch" of a glycoprotein preparation refers to a single production run of the glycoprotein. Evaluation of different batches thus means evaluation of different production runs or batches. As used herein, "sample(s)" refer to separately procured samples. For example, evaluation of separate samples could mean evaluation of different commercially available containers or vials of the same batch or from different batches.

As used herein, "ustekinumab" is the generic, compendial, nonproprietary, or official FDA name for the product marketed in the United States as STELARA® and a product that is interchangeable with or equivalent to the product marketed as STELARA®.

As used herein, "evaluating", e.g., in the evaluation/evaluating, identifying, and/or producing aspects disclosed herein means reviewing, considering, determining, assessing, analyzing, measuring, and/or detecting the presence, absence, level, and/or ratio of sialylated glycans and/or one or more ustekinumab-specific parameters in a glycoprotein preparation to provide information pertaining to the one or more ustekinumab-specific parameters. In some instances, evaluating can include performing a process that involves a physical change in a sample or another substance, e.g., a starting material. Exemplary changes include making a physical entity from two or more starting materials, shearing or fragmenting a substance, separating or purifying a substance, combining two or more separate entities into a mixture, performing a chemical reaction that includes breaking or forming a covalent or non-covalent bond. "Evaluating" can include performing an analytical process which includes a physical change in a substance, e.g., a sample, analyte, or reagent (sometimes referred to herein as "physical analysis"), performing an analytical method, e.g., a method which includes one or more of the following: separating or purifying a substance, e.g., an analyte, or a fragment or other derivative thereof, from another substance; combining an analyte, or fragment or other derivative thereof, with another substance, e.g., a buffer, solvent, or reactant; or changing the structure of an analyte, or a fragment or other derivative thereof, e.g., by breaking or forming a covalent or non-covalent bond, between a first and a second atom of the analyte; or by changing the structure of a reagent, or a fragment or other derivative thereof, e.g., by breaking or forming a covalent or non-covalent bond, between a first and a second atom of the reagent. In some instances, evaluating a glycoprotein preparation includes detecting the presence, absence, level or ratio of sialylated glycans and/or one or more (e.g., two or more when working with ratios) parameters disclosed in FIG. 3, e.g., using methods disclosed in Table 1.

Information (e.g., value(s)) pertaining to a "ustekinumab-specific parameter" or a "ustekinumab parameter" means information, regardless of form, that describes the presence, absence, abundance, absolute or relative amount, ratio (with another entity), or distribution of a moiety associated with the glycoprotein preparation and/or ustekinumab. Information is evaluated in a glycoprotein preparation as disclosed herein. Information is also conveyed in a ustekinumab signature. Information can be qualitative, e.g., present, absent, intermediate, or quantitative, e.g., a numerical value such as a single number, or a range, for a parameter. In some instances, information is from a single sample or batch or a plurality of samples or batches. In some instances, information can be a range or average (or other measure of central tendency), e.g., based on the values from any X samples or batches, e.g., wherein at least of the samples or batches is being evaluated for commercial release, wherein X is equal to, at least, or no more than, 2, 3, 4, 5, 6, 7, 8, 9, 10, 11, 12, 13, 14, 15, 16, 17, 18, 19, 20, 21, 22, 23 or 24. In some instances, information can be, for example: a statistical function, e.g., an average, of a number of values; a function of another value, e.g., of the presence, distribution or amount of a second entity present in the sample, e.g., an internal standard; a value, e.g., a qualitative value, e.g., present, absent, "below limit of detection", "within normal limits" or intermediate. In some instances, information can be a quantitative value, e.g., a numerical value such as a single number, a range of values, a "no less than x amount" value, a "no more than x amount" value. In some instances, information can be abundance. Abundance can be expressed in relative terms, e.g., abundance can be expressed in terms of the abundance of a structure in relation to another component in the preparation. E.g., abundance can be expressed as: the abundance of a structure (or a first group of structures) in FIG. 3 relative to the amount of protein; the abundance of a structure (or a first group of structures) in FIG. 3 relative to the abundance of a second structure (or second group of structures) in FIG. 3. Abundance, e.g., abundance of a first structure relative to another structure, can be with regard to the preparation as a whole, a single molecule, or a selected site on the protein backbone. E.g., the parameter can be the relative proportion of a first structure from FIG. 3 and a second structure from FIG. 3 at a selected site and the value can be expressed as, e.g., a proportion, ratio or percentage. Information can be expressed in any useful term or unit, e.g., in terms of weight/weight, number/number, number/weight, and weight/number. In many cases, the reference criterion is defined by a range of values.

As used herein, "acquire" or "acquiring" (e.g., "acquiring information") means obtaining possession of a physical entity, or a value, e.g., a numerical value, by "directly acquiring" or "indirectly acquiring" the physical entity or value. "Directly acquiring" means performing a process (e.g., performing an assay or test on a sample or "analyzing a sample" as that term is defined herein) to obtain the physical entity or value. "Indirectly acquiring" refers to receiving the physical entity or value from another party or source (e.g., a third party laboratory that directly acquired the physical entity or value). "Directly acquiring" a physical entity includes performing a process, e.g., analyzing a sample, that includes a physical change in a physical substance, e.g., a starting material. Exemplary changes include making a physical entity from two or more starting materials, shearing or fragmenting a substance, separating or purifying a substance, combining two or more separate entities into a mixture, performing a chemical reaction that includes breaking or forming a covalent or non-covalent bond. "Directly acquiring" a value includes performing a process that includes a physical change in a sample or another substance, e.g., performing an analytical process which includes a physical change in a substance, e.g., a sample, analyte, or reagent (sometimes referred to herein as "physical analysis"), performing an analytical method, e.g., a method which includes one or more of the following: separating or purifying a substance, e.g., an analyte, or a fragment or other derivative thereof, from another substance; combining an analyte, or fragment or other derivative thereof, with another substance, e.g., a buffer, solvent, or reactant; or changing the structure of an analyte, or a fragment or other derivative thereof, e.g., by breaking or forming a covalent or non-covalent bond, between a first and a second atom of the analyte; or by changing the structure of a reagent, or a fragment or other derivative thereof, e.g., by breaking or forming a covalent or non-covalent bond, between a first and a second atom of the reagent. Exemplary analytical methods are shown in Table 1.

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls. The section headings used herein are for organizational purposes only and are not to be construed as limiting the subject matter described in any way.

These, and other aspects of the invention, are described in more detail below and in the claims.

BRIEF DESCRIPTION OF THE DRAWINGS

FIG. 1 is the amino acid sequence of heavy chain of ustekinumab (SEQ ID NO:1).

FIG. 2 is the amino acid sequence of light chain of ustekinumab (SEQ ID NO:2).

FIG. 3 is a table depicting four ustekinumab parameters.

DETAILED DESCRIPTION

Figure 4:
FIG. 4 is a table depicting the structures of the sialylated glycans and their percentage of detection relative to the total number of identified glycans for an illustrative sample of ustekinumab.

Detailed, high resolution, physiochemical and/or structural information about STELARA® (e.g., related to the presence and/or level(s) of signature species) can be used in the manufacture of products that qualify as ustekinumab, e.g., that are biosimilar or interchangeable versions of STELARA®. Such information is also useful in monitoring product changes and controlling structural drift that may occur as a result of manufacturing changes. The art supports, however, that information necessary to be able to make and test products that qualify as ustekinumab, e.g., that are interchangeable versions of STELARA®, or any other branded biologic, is unavailable (see, e.g., Nowicki, "Basic Facts about Biosimilars," Kidney Blood Press. Res., 30:267-272 (2007); Hincal "An Introduction To Safety Issues In Biosimilars/Follow-On Biopharmaceuticals", J. Med. CBR Def., 7:1-18, (2009); Roger, "Biosimilars: current status and future directions," Expert Opin. Biol. Ther., 10(7):1011-1018 (2010); Schellekens et al., Nat. Biotechnol. 28:28-31 (2010); Sekhon et al., Biosimilars, 1:1-11 (2011)). One exemplary report states that "[t]he size and complexity of . . . therapeutic proteins make the production of an exact replica almost impossible; therefore, there are no true generic forms of these proteins . . . Verification of the similarity of biosimilars to innovator medicines remains a key challenge" (Hincal, supra). This disclosure provides, in part, methods and compositions sufficient to make and test products that qualify as ustekinumab, e.g., that are biosimilar and/or interchangeable versions of STELARA®.

In some instances, providing or obtaining a glycoprotein preparation (e.g., such as a glycoprotein drug substance or a precursor thereof), e.g., that is or includes a glycoprotein, can include providing a host cell, e.g., a mammalian host cell (e.g., a Sp2/0 murine myeloma cell) that is genetically engineered to express a glycoprotein having an amino acid sequence at least 85% identical to SEQ ID NO:1 (or to SEQ ID NO:1 lacking 1-5 amino acid residues at the amino and/or carboxyl terminus) and an amino acid sequence at least 85% identical to SEQ ID NO:2 (or to SEQ ID NO:2 lacking 1-5 amino acid residues at the amino and/or carboxyl terminus) (e.g., a genetically engineered cell); culturing the host cell under conditions suitable to express the glycoprotein (e.g., mRNA and/or protein); and, optionally, purifying the expressed glycoproteins (e.g., in the form of a recombinant antibody) from the cultured cell, thereby producing a glycoprotein preparation. In some instances, the host cell is genetically engineered to express a glycoprotein having an amino acid sequence at least 90%, 91%, 92%, 93%, 94%, 95%, 96%, 97%, 98%, 99%, or 100% identical to SEQ ID NO:1 and an amino acid sequence at least 90%, 91%, 92%, 93%, 94%, 95%, 96%, 97%, 98%, 99%, or 100% identical to SEQ ID NO:2, wherein the expressed amino acid sequences form a recombinant antibody composition. In other instances, a glycoprotein preparation is obtainable using another method known in the field and/or is provided by a party (e.g., a third party).

As used herein "percent (%) sequence identity" with respect to a sequence is defined as the percentage of amino acid residues or nucleotides in a candidate sequence that are identical with the amino acid residues or nucleotides in the reference sequence, after aligning the sequences and introducing gaps, if necessary, to achieve the maximum percent sequence identity. (E.g., gaps can be introduced in one or both of a first and a second amino acid or nucleic acid sequence for optimal alignment and non-homologous sequences can be disregarded for comparison purposes).

Alignment for purposes of determining percent sequence identity can be achieved in various ways that are within the skill in the art, for instance, using publicly available computer software such as BLAST, ALIGN or Megalign (DNASTAR) software. Those skilled in the art can determine appropriate parameters for measuring alignment, including any algorithms needed to achieve maximal alignment over the full length of the sequences being compared. In one embodiment, the length of a reference sequence aligned for comparison purposes is at least 30%, e.g., at least 40%, e.g., at least 50%, 60%, 70%, 80%, 90%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. In some instances a product will include amino acid variants, e.g., species that differ at terminal residues, e.g., at one or two terminal residues. In instances of such cases the sequence identity which is compared is the identity between the primary amino acid sequences of the most abundant active species in each of the products being compared. In some instances sequence identity refers to the amino acid sequence encoded by a nucleic acid that can be used to make the product.

In some instances, a ustekinumab signature disclosed herein can include a level of sialylated glycans of about 10%, 15%, 20%, 25% 30%, 35%, 40%, 50%, 10-20%, 20-30%, 30-40%, 40-50%, 10-50%, 20-50%, 30-50%, 40-50%, or 25-35%.

In some instances, a ustekinumab signature disclosed herein can include 1, 2, 3, or 4 of the ustekinumab parameters shown in FIG. 3 (e.g., including any combination of 2 or more (e.g., 3 or 4) of parameter numbers 1-4 shown in FIG. 3). In some instances, a ustekinumab signature disclosed herein can include one or more of about 5-20% (e.g., about 5-10%, 10-20%, 7-12%, 5%, 6%, 7%, 8%, 9%, 10%, 11%, 12%, 13%, 14%, or 15%) of parameter 1 shown in FIG. 3 about 2-10% (e.g., about 2-5%, 5-10%, 3-7%, 2%, 3%, 4%, 5%, 6%, 7%, 8%, 9%, or 10%) of parameter 2 shown in FIG. 3; about 5-20% (e.g., about 5-10%, 10-20%, 7-12%, 5%, 6%, 7%, 8%, 9%, 10%, 11%, 12%, 13%, 14%, or 15%) of parameter 3 shown in FIG. 3; and about 0.5-5% (e.g., about 0.5-2.5%, 2.5-5%, 0.5%, 1%, 1.5%, 2%, or 2.5%) of parameter 4 shown in FIG. 3. In some instances, a ustekinumab signature includes the reference criterion for one or more of parameters 1-4 shown in FIG. 3.

In some instances, the present disclosure includes determining whether information evaluated for a glycoprotein preparation meets a ustekinumab signature, e.g., by comparing the information with the ustekinumab signature and/or confirming that the information has a defined (e.g., predefined) relationship with the ustekinumab signature.

In some instances, methods disclosed herein can be used to confirm the identity and/or quality of ustekinumab preparations. For example, methods can include assessing preparations (e.g., samples, lots, and/or batches) of a test glycoprotein to confirm whether the test glycoprotein qualifies as ustekinumab, and, optionally, qualifying the test protein as ustekinumab if qualifying criteria (e.g. predefined qualifying criteria) are met; thereby evaluating, identifying, and/or producing (e.g., manufacturing) ustekinumab.

Methods of the disclosure have a variety of applications and include, e.g., quality control at different stages of manufacture, analysis of ustekinumab preparations prior to or after completion of manufacture (e.g., prior to or after distribution to a fill/finish environment or facility), prior to or after release into commerce (e.g., before distribution to a pharmacy, a caregiver, a patient, or other end-user). Thus, the preparation can be any preparation that potentially comprises ustekinumab. In an embodiment the ustekinumab preparation is a drug substance (an active pharmaceutical ingredient or "API") or a drug product (an API formulated for use in a subject such as a human patient). In an embodiment the preparation is from a stage of manufacture or use that is prior to release to care givers or other end-users; prior to packaging into individual dosage forms, such as syringes, pens, vials, or multi-dose vials; prior to determination that the batch can be commercially released, prior to production of a Certificate of Testing, Material Safety Data Sheet (MSDS) or Certificate of Analysis (CofA) of the preparation. In an embodiment the glycoprotein preparation is from an intermediate step in production, e.g., it is after secretion of the glycoprotein from a cell but prior to purification of drug substance.

Evaluations from methods of the disclosure are useful, e.g., for guiding, controlling or implementing a number of activities or steps in the process of making, distributing, and monitoring and providing for the safe and efficacious use of ustekinumab. Thus, in an embodiment, e.g., responsive to the evaluation, e.g., depending on whether a criterion is met, a decision or step is taken. The method can further comprise one or both of the decision to take the step and/or carrying out the step itself. E.g., the step can comprise one in which the preparation (or another preparation for which the preparation is representative) is: classified; selected; accepted or discarded; released or processed into a drug product; rendered unusable for commercial release, e.g., by labeling it, sequestering it, or destroying it; passed on to a subsequent step in manufacture; reprocessed (e.g., the preparation may undergo a repetition of a previous process step or subjected to a corrective process); formulated, e.g., into drug substance or drug product; combined with another component, e.g., an excipient, buffer or diluent; disposed into a container; divided into smaller aliquots, e.g., unit doses, or multi-dose containers; combined with another preparation of ustekinumab; packaged; shipped; moved to a different location; combined with another element to form a kit; combined, e.g., placed into a package with a delivery device, diluent, or package insert; released into commerce; sold or offered for sale; delivered to a care giver or other end-user; or administered to a subject. E.g., based on the result of the determination or whether one or more subject entities is present, or upon comparison to a reference standard, the batch from which the preparation is taken can be processed, e.g., as just described.

Methods described herein may include making a decision: (a) as to whether a preparation may be formulated into drug substance or drug product; (b) as to whether a preparation may be reprocessed (e.g., the preparation may undergo a repetition of a previous process step); or (c) that the preparation is not suitable for formulation into drug substance or drug product. In instances the method comprises: formulating as referred to in step (a), reprocessing as referred to in step (b), or rendering the preparation unusable for commercial release, e.g., by labeling it or destroying it, as referred to in step (c).

Parameter Evaluation

The amino acid sequence of the heavy chain of ustekinumab (STELARA®) is disclosed herein as SEQ ID NO:1. The amino acid sequence of the light chain of ustekinumab (STELARA®) is disclosed herein as SEQ ID NO:2.

Parameters disclosed herein can be analyzed by any available suitable method. In some instances, glycan structure and composition as described herein are analyzed, for example, by one or more, enzymatic, chromatographic, mass spectrometry (MS), chromatographic followed by MS, electrophoretic methods, electrophoretic methods followed by MS, nuclear magnetic resonance (NMR) methods, and combinations thereof. Exemplary enzymatic methods include contacting a glycoprotein preparation with one or more enzymes under conditions and for a time sufficient to release one or more glycans (e.g., one or more exposed glycans). In some instances, the one or more enzymes include PNGase F. Exemplary chromatographic methods include, but are not limited to, Strong Anion Exchange chromatography using Pulsed Amperometric Detection (SAX-PAD), liquid chromatography (LC), high performance liquid chromatography (HPLC), ultra performance liquid chromatography (UPLC), thin layer chromatography (TLC), amide column chromatography, and combinations thereof. Exemplary mass spectrometry (MS) include, but are not limited to, tandem MS, LC-MS, LC-MS/MS, matrix assisted laser desorption ionisation mass spectrometry (MALDI-MS), Fourier transform mass spectrometry (FTMS), ion mobility separation with mass spectrometry (IMS-MS), electron transfer dissociation (ETD-MS), and combinations thereof. Exemplary electrophoretic methods include, but are not limited to, capillary electrophoresis (CE), CE-MS, gel electrophoresis, agarose gel electrophoresis, acrylamide gel electrophoresis, SDS-polyacrylamide gel electrophoresis (SDS-PAGE) followed by Western blotting using antibodies that recognize specific glycan structures, and combinations thereof. Exemplary nuclear magnetic resonance (NMR) include, but are not limited to, one-dimensional NMR (1D-NMR), two-dimensional NMR (2D-NMR), correlation spectroscopy magnetic-angle spinning NMR (COSY-NMR), total correlated spectroscopy NMR (TOCSY-NMR), heteronuclear single-quantum coherence NMR (HSQC-NMR), heteronuclear multiple quantum coherence (HMQC-NMR), rotational nuclear overhauser effect spectroscopy NMR (ROESY-NMR), nuclear overhauser effect spectroscopy (NOESY-NMR), and combinations thereof.

In some instances, techniques described herein may be combined with one or more other technologies for the detection, analysis, and or isolation of glycans or glycoproteins. For example, in certain instances, glycans are analyzed in accordance with the present disclosure using one or more available methods (to give but a few examples, see Anumula, Anal. Biochem., 350(1):1, 2006; Klein et al., Anal. Biochem., 179:162, 1989; and/or Townsend, R. R. Carbohydrate Analysis" High Performance Liquid Chromatography and Capillary Electrophoresis., Ed. Z. El Rassi, pp 181-209, 1995; WO2008/128216; WO2008/128220; WO2008/128218; WO2008/130926; WO2008/128225; WO2008/130924; WO2008/128221; WO2008/128228; WO2008/128227; WO2008/128230; WO2008/128219; WO2008/128222; WO2010/071817; WO2010/071824; WO2010/085251; WO2011/069056; and WO2011/127322, each of which is incorporated herein by reference in its entirety). For example, in some instances, glycans are characterized using one or more of chromatographic methods, electrophoretic methods, nuclear magnetic resonance methods, and combinations thereof. In some embodiments, glycans are analyzed by labeling with a fluorescent dye and measuring levels of fluorescence.

In some instances, methods for evaluating one or more ustekinumab-specific parameters, e.g., in a glycoprotein preparation, e.g., one or more of ustekinumab parameters disclosed in FIG. 3 in a glycoprotein preparation are known in the art and/or are disclosed in Table 1:

TABLE 1

| Method(s) | Relevant literature | Parameter |
|---|---|---|
| C18 UPLC Mass Spec. | Chen and Flynn, Anal. Biochem., 370: 147-161 (2007) Chen and Flynn, J. Am. Soc. Mass Spectrom., 20: 1821-1833 (2009) | Glycan(s) (e.g., N-linked glycan, exposed N-linked glycan, glycan detection, glycan identification, and characterization; site specific glycation; glycoform detection (e.g., parameters 1-4); percent glycosylation; and/or aglycosyl) |
| HILIC UPLC Mass Spec. | Shang et al., J. Pharm. Sci. 103: 1967-1978 (2014) | Glycan(s) (e.g., N-linked glycan, exposed N-linked glycan, glycan detection, glycan identification, and characterization; site specific glycation; glycoform detection (e.g., parameters 1-4); percent glycosylation; and/or aglycosyl) |
| Bioanalyzer (reducing/non-reducing) | Forrer et al., Anal. Biochem., 334: 81-88 (2004) | Glycan (e.g., N-linked glycan, exposed N-linked glycan) (including, for example, glycan detection, identification, and characterization; site specific glycation; glycoform detection; percent glycosylation; and/or aglycosyl) |
| LC-MS (reducing/non-reducing/alkylated)* *Methods include removal (e.g., enzymatic, chemical, and physical) of glycans | Dick et al., Biotechnol. Bioeng., 100: 1132-1143 (2008) Goetze et al., Glycobiol., 21: 949-959 (2011) Xie et al., mAbs, 2: 379-394 (2010) | Glycan (e.g., N-linked glycan, exposed N-linked glycan) (including, for example, glycan detection, identification, and characterization; site specific glycation; glycoform detection; percent glycosylation; and/or aglycosyl) |
| Anion-exchange chromatography | Ahn et al., J. Chrom. B, 878: 403-408 (2010) | Sialylated glycan |
| 1,2-diamino-4,5-methylenedioxybenzene (DMB) labeling method | Hokke et al., FEBS Lett., 275: 9-14 (1990) | Sialic acid |

Literature shown in Table 1 are hereby incorporated by reference in their entirety or, in the alternative, to the extent that they pertain to one or more of the methods disclosed in Table 1.

Recombinant Gene Expression

In accordance with the present disclosure, there may be employed conventional molecular biology, microbiology, and recombinant DNA techniques within the skill of the art. Such techniques are described in the literature (see, e.g., Sambrook, Fritsch & Maniatis, Molecular Cloning: A Laboratory Manual, Second Edition (1989) Cold Spring Harbor Laboratory Press, Cold Spring Harbor, N.Y.; DNA Cloning: A Practical Approach, Volumes I and II (D. N. Glover ed. 1985); Oligonucleotide Synthesis (M. J. Gait ed. 1984); Nucleic Acid Hybridization (B. D. Hames & S. J. Higgins eds. (1985)); Transcription And Translation (B. D. Hames & S. J. Higgins, eds. (1984)); Animal Cell Culture (R. I. Freshney, ed. (1986)); Immobilized Cells and Enzymes (IRL Press, (1986)); B. Perbal, A Practical Guide To Molecular Cloning (1984); F. M. Ausubel et al. (eds.), Current Protocols in Molecular Biology, John Wiley & Sons, Inc. (1994).

Recombinant expression of a gene, such as a gene encoding a glycoprotein described herein, can include construction of an expression vector containing a polynucleotide that encodes the glycoprotein. Once a polynucleotide has been obtained, a vector for the production of the glycoprotein can be produced by recombinant DNA technology using techniques known in the art. Known methods can be used to construct expression vectors containing polypeptide coding sequences and appropriate transcriptional and translational control signals. These methods include, for example, in vitro recombinant DNA techniques, synthetic techniques, and in vivo genetic recombination.

An expression vector can be transferred to a host cell by conventional techniques, and the transfected cells can then be cultured by conventional techniques to produce glycoproteins.

A variety of host expression vector systems can be used (see, e.g., U.S. Pat. No. 5,807,715). Such host-expression systems can be used to produce polypeptides and, where desired, subsequently purified. Such host expression systems include microorganisms such as bacteria (e.g., *E. coli* and *B. subtilis*) transformed with recombinant bacteriophage DNA, plasmid DNA or cosmid DNA expression vectors containing polypeptide coding sequences; yeast (e.g., *Saccharomyces* and *Pichia*) transformed with recombinant yeast expression vectors containing polypeptide coding sequences; insect cell systems infected with recombinant virus expression vectors (e.g., baculovirus) containing polypeptide coding sequences; plant cell systems infected with recombinant virus expression vectors (e.g., cauliflower mosaic virus, CaMV; tobacco mosaic virus, TMV) or transformed with recombinant plasmid expression vectors (e.g. Ti plasmid) containing polypeptide coding sequences; or mammalian cell systems (e.g., COS, CHO, BHK, 293, NS0, and 3T3 cells), e.g., harboring recombinant expression constructs containing promoters derived from the genome of mammalian cells (e.g., metallothionein promoter) or from mammalian viruses (e.g., the adenovirus late promoter; the vaccinia virus 7.5K promoter).

For expression in mammalian host cells, viral-based expression systems can be utilized (see, e.g., Logan & Shenk, 1984, Proc. Natl. Acad. Sci. USA 8 1:355-359). The efficiency of expression can be enhanced by the inclusion of appropriate transcription enhancer elements, transcription terminators, etc. (see, e.g., Bittner et al., 1987, Methods in Enzymol. 153:516-544).

In addition, a host cell strain can be chosen that modulates the expression of the inserted sequences, or modifies and processes the gene product in the specific fashion desired. Different host cells have characteristic and specific mechanisms for the post-translational processing and modification of proteins and gene products. Appropriate cell lines or host systems can be chosen to ensure the correct modification and processing of the polypeptide expressed. Such cells include, for example, established mammalian cell lines and insect cell lines, animal cells, fungal cells, and yeast cells. Mammalian host cells include, but are not limited to, CHO, VERY, BHK, HeLa, COS, MDCK, 293, 3T3, W138, BT483, Hs578T, HTB2, BT20 and T47D, NS0 (a murine myeloma cell line that does not endogenously produce any immunoglobulin chains), CRL7O3O and HsS78Bst cells.

For long-term, high-yield production of recombinant proteins, host cells are engineered to stably express a polypeptide. Host cells can be transformed with DNA controlled by appropriate expression control elements known in the art, including promoter, enhancer, sequences, transcription terminators, polyadenylation sites, and selectable markers. Methods commonly known in the art of recombinant DNA technology can be used to select a desired recombinant clone.

Once a glycoprotein described herein been produced by recombinant expression, it may be purified by any method known in the art for purification, for example, by chromatography (e.g., ion exchange, affinity, and sizing column chromatography), centrifugation, differential solubility, or by any other standard technique for the purification of proteins. For example, an antibody can be isolated and purified by appropriately selecting and combining affinity columns such as Protein A column with chromatography columns, filtration, ultra-filtration, salting-out and dialysis procedures (see Antibodies: A Laboratory Manual, Ed Harlow, David Lane, Cold Spring Harbor Laboratory, 1988). Further, as described herein, a glycoprotein can be fused to heterologous polypeptide sequences to facilitate purification. Glycoproteins having desired sugar chains can be separated with a lectin column by methods known in the art (see, e.g., WO 02/30954).

The disclosure is further illustrated by the following examples. The examples are provided for illustrative purposes only. They are not to be construed as limiting the scope or content of the disclosure in any way.

EXAMPLES

Example 1: Characterization of Ustekinumab

Three lots of ustekinumab (STELARA®) were subjected to glycan analysis, and the levels of sialylated glycans were measured. FIG. 4 depicts the structures of the sialylated glycans and their percentage of detection relative to the total number of identified glycans for an illustrative sample of ustekinumab.

The results of the glycan analysis showed an unexpectedly high percentage (mol/mol) of total sialylated glycans. The information (values) shown for each glycan structure in FIG. 4 were used to formulate ustekinumab parameters and a reference criterion or rule for each (shown in FIG. 3).

Example 2: Process in Manufacturing of Ustekinumab Drug Product

A sample of a batch of a test glycoprotein drug substance, comprising a recombinant antibody composition having a first amino acid sequence with at least 98% identity to SEQ ID NO:1 and a second amino acid sequence with at least 98% identity to SEQ ID NO:2, is obtained. The level of sialylated glycans of the test glycoprotein sample is acquired, and the level of sialyated glycans is about 10-50%. Accordingly, at least a portion of the batch of the test glycoprotein drug substance is processed as drug product.

Example 3: Process in Manufacturing of Ustekinumab Drug Product

A sample of a batch of a test glycoprotein drug substance, comprising a recombinant antibody composition having a first amino acid sequence with at least 98% identity to SEQ ID NO:1 and a second amino acid sequence with at least 98% identity to SEQ ID NO:2, is obtained. The level of sialylated glycans of the test glycoprotein sample is acquired, and the level of sialyated glycans is not about 10-50%. Accordingly, the batch of the test glycoprotein drug substance is disposed of, is classified for disposal, is labeled for disposal, or is reprocessed.

EQUIVALENTS

It is to be understood that while the disclosure has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of manufacturing a drug product, comprising:
providing a host cell that is genetically engineered to express a first amino acid sequence having a sequence of SEQ ID NO:1 and a second amino acid sequence having a sequence of SEQ ID NO:2;
culturing the host cell under conditions whereby the cell expresses the first and second amino acid sequences, wherein the expressed first and second amino acid sequences form recombinant antibodies;
harvesting a plurality of recombinant antibodies from the host cell culture to produce an antibody preparation;
measuring an amount of sialylated glycans for one or more of Glycan 1, Glycan 2, Glycan 3, and Glycan 4 for the antibody preparation, wherein the amount of sialylated glycans is measured by a method selected from C18 UPLC mass spectrometry, HILIC UPLC mass spectrometry, reducing/non-reducing bioanalyzer, reducing/non-reducing LC-MS, anionexchange chromatography 1,2-diamino-4,5-methylenedioxybenzene (DMB) labeling method, or any combination thereof: and
processing at least a portion of the antibody preparation as a drug product if the measured amount of sialylated glycans is 5-20%, for Glycan 1, 2-10%, for Glycan 2, 5-20% for Glycan 3, and/or 0.5-5% for Glycan 4; and
producing the drug product comprising the at least a portion of the antibody preparation having the measured amount of sialylated glycans.

2. The method of claim 1, comprising measuring an amount for two or more of Glycan 1, Glycan 2, Glycan 3, and Glycan 4 for the antibody preparation and processing at least a portion of the antibody preparation as drug product if the measured amount for Glycan 1 is 5-20%, the measured amount for Glycan 2 is 2-10%, the measured amount for Glycan 3 is 5-20%, and/or the measured amount for Glycan 4 is 0.5-5%.

3. The method of claim 1, comprising measuring an amount for three or more of Glycan 1, Glycan 2, Glycan 3, and Glycan 4 for the antibody preparation and processing at least a portion of the antibody preparation as drug product if the measured amount for Glycan 1 is 5-20%, the measured amount for Glycan 2 is 2-10%, the measured amount for Glycan 3 is 5-20%, and/or the measured amount for Glycan 4 is 0.5-5%.

4. The method of claim 1, comprising measuring an amount for Glycan 1, Glycan 2, Glycan 3, and Glycan 4 for the antibody preparation and processing at least a portion of the antibody preparation as drug product if the measured amount for Glycan 1 is 5-20%, the measured amount for Glycan 2 is 2-10%, the measured amount for Glycan 3 is 5-20%, and/or the measured amount for Glycan 4 is 0.5-5%.

5. The method of claim 1, comprising measuring an amount for Glycans 1 and 2 for the antibody preparation and processing at least a portion of the antibody preparation as drug product if a ratio of the measured amount for Glycan 1 to the measured amount for Glycan 2 is greater than 1.5, 2, 2.5, 3, 3.5, 4, 4.5, 5, or greater.

6. The method of claim 1, comprising measuring and amount for Glycans 2 and 3 for the antibody preparation and processing at least a portion of the antibody preparation as drug product if a ratio of the measured amount for Glycan 2 to the measured amount for Glycan 3 is less than 0.5, 0.4, 0.3, 0.2, 0.1, 0.075, 0.05, or 0.025.

7. The method of claim 1, comprising measuring an amount for Glycans 3 and 4 for the antibody preparation and processing at least a portion of the antibody preparation as drug product if a ratio of the measured amount for Glycan 3 to the measured amount for Glycan 4 is greater than 5, 6, 7, 8, 9, 10, 11, 12, 13, 14, or 15.

8. The method of claim 1, comprising measuring an amount for Glycans 1 and 3 for the antibody preparation and processing at least a portion of the antibody preparation as drug product if a ratio of the measured amount for Glycan 1 to the measured amount for Glycan 3 is 0.5, 0.6, 0.7, 0.8, 0.9, 1, 1.1, 1.2, 1.3, 1.4, or 1.5.

9. The method of claim 1, comprising measuring an amount for Glycans 1 and 4 for the antibody preparation and processing at least a portion of the antibody preparation as drug product if a ratio of the measured amount for Glycan 1 to the measured amount for Glycan 4 is greater than 5, 6, 7, 8, 9, 10, 11, 12, 13, 14, or 15.

10. The method of claim 1, comprising measuring an amount for Glycans 2 and 4 for the antibody preparation and processing at least a portion of the antibody preparation as drug product if a ratio of the measured amount for Glycan 2 to the measured amount for Glycan 4 is greater than 4, 5, 6, 7, 8, 9, 10, 11, or 12.

11. The method of claim 1, wherein the drug product further comprises an excipient or buffer.

12. The method of claim 1, wherein the drug product is approved under Section 351(k) of the Public Health Service (PHS) Act.

13. The method of claim 1, wherein the drug product is not approved under biologics license application (BLA) under Section 351(a) of the Public Health Service (PHS) Act.

14. The method of claim 1, wherein the measured amount of sialylated glycans for the antibody preparation comprises an average of two or more amounts from multiple batches or samples of the antibody preparation.

\* \* \* \* \*

SEQUENCE LISTING

```
Sequence total quantity: 2
SEQ ID NO: 1          moltype = AA   length = 449
FEATURE               Location/Qualifiers
REGION                1..449
                      note = Description of Artificial Sequence: Synthetic
                      polypeptide
source                1..449
                      mol_type = protein
                      organism = synthetic construct
SEQUENCE: 1
EVQLVQSGAE VKKPGESLKI SCKGSGYSFT TYWLGWVRQM PGKGLDWIGI MSPVDSDIRY    60
SPSFQGQVTM SVDKSITTAY LQWNSLKASD TAMYYCARRR PGQGYFDFWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSRDEL   360
```

```
                               -continued

TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                    449

SEQ ID NO: 2            moltype = AA  length = 165
FEATURE                 Location/Qualifiers
REGION                  1..165
                        note = Description of Artificial Sequence: Synthetic
                         polypeptide
source                  1..165
                        mol_type = protein
                        organism = synthetic construct
SEQUENCE: 2
DIQMTQSPSS LSASVGDRVT ITCRASQGIS SWLAWYQQKP EKAPKSLIYA ASSLQSGVPS   60
RFSGSGSGTD FTLTISSLQE DFATYYCQQY NIYPYTFGQG TKLEIKRTVA APSVFIFPPS   120
DEQLKSGTAS VVCLLNNFYP REAKVQWKVD NALQSGNSQE SVTEQ                  165
```